United States Patent
Ichikawa et al.

(10) Patent No.: US 12,137,879 B2
(45) Date of Patent: Nov. 12, 2024

(54) IMAGE PROCESSING APPARATUS, IMAGE PROCESSING METHOD, AND ENDOSCOPE APPARATUS

(71) Applicant: OLYMPUS CORPORATION, Hachioji (JP)

(72) Inventors: Manabu Ichikawa, Hachioji (JP); Toshiyuki Fujii, Hachioji (JP); Hiroaki Kagawa, Hachioji (JP); Osamu Nonaka, Hachioji (JP)

(73) Assignee: OLYMPUS CORPORATION, Hachioji (JP)

( * ) Notice: Subject to any disclaimer, the term of this patent is extended or adjusted under 35 U.S.C. 154(b) by 192 days.

(21) Appl. No.: 17/879,197

(22) Filed: Aug. 2, 2022

(65) Prior Publication Data
US 2022/0361739 A1    Nov. 17, 2022

Related U.S. Application Data

(63) Continuation of application No. PCT/JP2020/004370, filed on Feb. 5, 2020.

(51) Int. Cl.
*A61B 1/06* (2006.01)
*A61B 1/00* (2006.01)

(52) U.S. Cl.
CPC ........ *A61B 1/0638* (2013.01); *A61B 1/00009* (2013.01); *A61B 1/0646* (2013.01)

(58) Field of Classification Search
CPC .. A61B 1/0638; A61B 1/00009; A61B 1/0646
USPC ......................................................... 348/65
See application file for complete search history.

(56) References Cited

U.S. PATENT DOCUMENTS

| | | | |
|---|---|---|---|
| 2012/0302847 A1 | 11/2012 | Ozawa et al. | |
| 2019/0253615 A1 | 8/2019 | Fukuya et al. | |

FOREIGN PATENT DOCUMENTS

| | | |
|---|---|---|
| EP | 2526854 A1 | 11/2012 |
| JP | S58-029439 A | 2/1983 |
| JP | H08-018861 A | 1/1996 |
| JP | H09-005643 A | 1/1997 |
| JP | 2000-032442 A | 1/2000 |
| JP | 4121845 B2 | 7/2008 |
| JP | 2010-178766 A | 8/2010 |
| JP | 2012-239816 A | 12/2012 |

(Continued)

OTHER PUBLICATIONS

International Search Report dated Apr. 7, 2020, issued in counterpart Application No. PCT/JP2020/004370, with English Translation. (4 pages).

*Primary Examiner* — Nguyen T Truong
(74) *Attorney, Agent, or Firm* — WHDA, LLP

(57) ABSTRACT

An image processing apparatus includes an inference part which is capable of inference by using a first inference model for finding of a specific target object and by using a second inference model for discrimination about the specific target object and a control unit to which a first picked-up image obtained under a first image pickup condition and a second picked-up image obtained under a second image pickup condition different from the first image pickup condition can be inputted and which performs control such that in a case where the first picked-up image is inputted, the inference part is caused to execute inference by using the first inference model, and in a case where the second picked-up image is inputted, the inference part is caused to execute inference by using the second inference model.

12 Claims, 14 Drawing Sheets

(56) References Cited

FOREIGN PATENT DOCUMENTS

| | | |
|---|---|---|
| JP | 6256872 B2 | 1/2018 |
| JP | 2019-028876 A | 2/2019 |
| JP | 2019-042156 A | 3/2019 |
| JP | 2019-140561 A | 8/2019 |
| JP | 2019-216848 A | 12/2019 |
| WO | 2020/003992 A1 | 1/2020 |
| WO | 2020/012872 A1 | 1/2020 |
| WO | 2020/031851 A1 | 2/2020 |

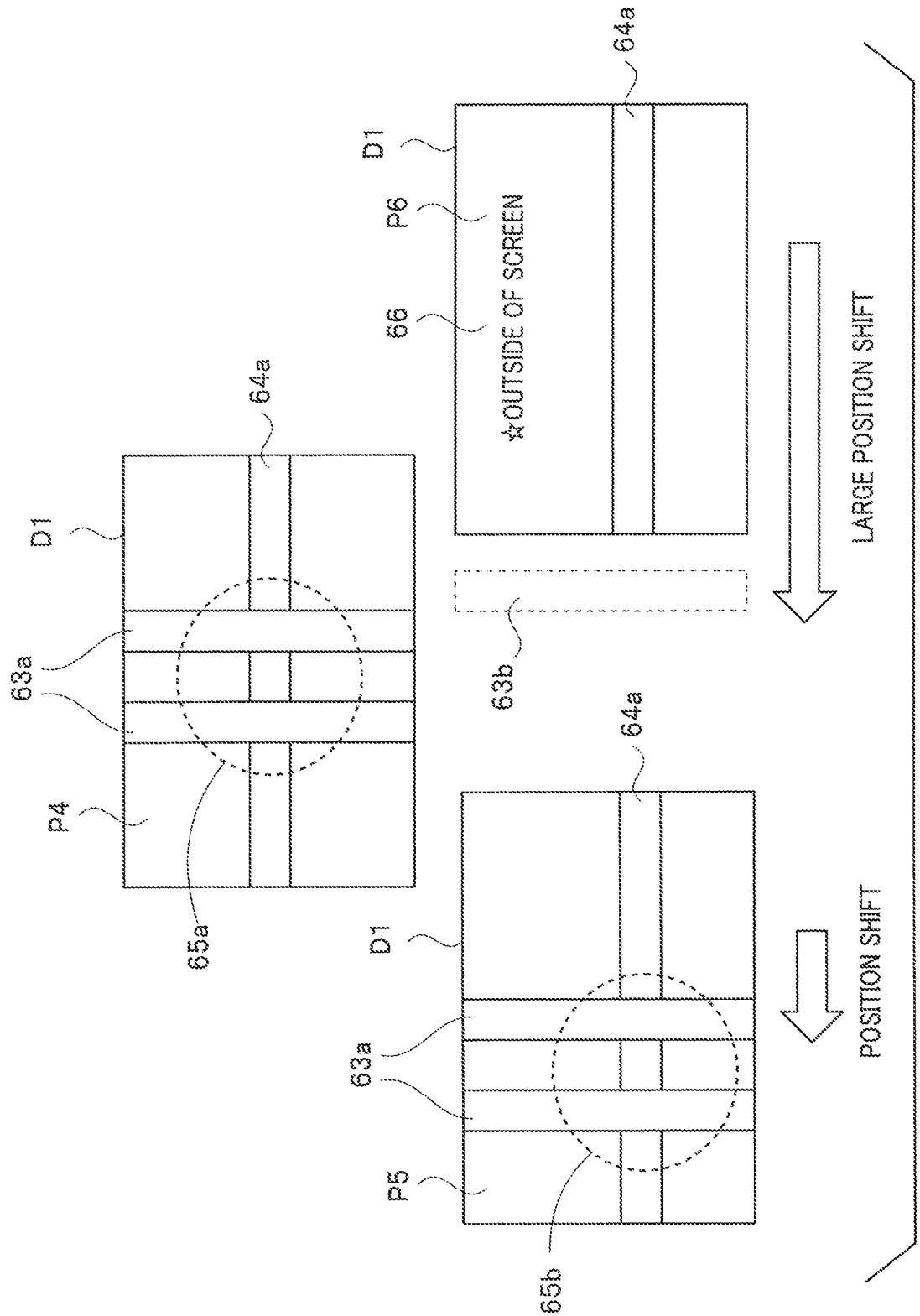

IMAGE PROCESSING APPARATUS, IMAGE PROCESSING METHOD, AND ENDOSCOPE APPARATUS

CROSS REFERENCE TO RELATED APPLICATION

This application is a continuation application of PCT/JP2020/004370 filed on Feb. 5, 2020, the entire contents of which are incorporated herein by this reference.

BACKGROUND OF THE INVENTION

1. Field of the Invention

The present invention relates to an image processing apparatus, an image processing method, and an endoscope apparatus in which precision of inference is improved regardless of a use form.

2. Description of the Related Art

In recent years, a technique in which a determination visually performed by a person is supported based on image data by utilizing AI (artificial intelligence) has progressed in each field.

There are many cases where in order to realize the above AI, a large amount of training data as input-output data sets serving as answers are prepared in advance and a technique referred to as deep learning is combined with the training data. In deep learning, "learning" for calculating a weight for appropriately deriving a solution to an unknown input is first performed by using the training data, and "inference" for deriving the solution to the input is performed by using the weight calculated by learning.

Note that in Japanese Patent Application Laid-Open Publication No. 2019-42156, for example, for a medical purpose, two analysis results about first and second medical images are enabled to be displayed such that positions, ranges (sizes), or the like can be compared, and checking of the analysis results is thereby made easy.

SUMMARY OF THE INVENTION

An image processing apparatus of one aspect of the present invention includes: a memory device that stores an inference part; and a control unit that performs a detection process based on the inference part, wherein: the inference part is capable of inference by using a first inference model for finding of a specific target object and by using a second inference model for discrimination about the specific target object; and the control unit is capable of receiving input of a first picked-up image obtained under a first image pickup condition and a second picked-up image obtained under a second image pickup condition different from the first image pickup condition and performing control such that in a case where the first picked-up image is inputted, the inference part is caused to execute inference by using the first inference model, and in a case where the second picked-up image is inputted, the inference part is caused to execute inference by using the second inference model.

An endoscope apparatus of one aspect of the present invention includes: a control unit which acquires picked-up images obtained by an image pickup apparatus configured to perform image pickup by illuminating a target object and performs control such that the image pickup apparatus performs image pickup under a first image pickup condition and a second image pickup condition different from the first image pickup condition; and an inference part which performs inference by a first inference model for finding of the target object and by a second inference model for discrimination about the target object, wherein the control unit receives, from the image pickup apparatus, an input of a first picked-up image obtained by performing image pickup under a first illumination condition or the first image pickup condition and an input of a second picked-up image obtained by performing image pickup under a second illumination condition or the second image pickup condition and performs control such that in a case where the first picked-up image is inputted, the inference part is caused to execute the inference by using the first inference model, and in a case where the second picked-up image is inputted, the inference part is caused to execute the inference by using the second inference model.

An image processing method of one aspect of the present invention includes: receiving a first picked-up image obtained under a first image pickup condition or a second picked-up image obtained under a second image pickup condition different from the first image pickup condition; and performing control such that in a case where the first picked-up image is inputted, inference by using a first inference model for finding of a specific target object is caused to be executed, and in a case where a second picked-up image is inputted, inference by using a second inference model for discrimination about the specific target object is caused to be executed.

BRIEF DESCRIPTION OF THE DRAWINGS

FIG. 14 is an explanatory diagram for explaining the third embodiment of the present invention.

DETAILED DESCRIPTION OF THE PREFERRED EMBODIMENTS

Embodiments of the present invention will hereinafter be described with reference to drawings.

First Embodiment

In recent years, in endoscope examinations of stomach, large intestine, esophagus, and so forth, development of techniques for supporting diagnoses by doctors by utilizing AI (artificial intelligence) has actively been performed. For example, computer aided detection (CADe) for detecting a lesion from an image photographed at a medical site and a computer aided diagnosis (CADx) for detecting a suspected disease name, a possibility of the disease, or the like are present. Note that the CADe and CADx may also collectively be referred to as CAD (computer aided diagnosis). The CAD is an examination which is performed by observing blood vessels in an inner portion non-invasively to a mucosa of a digestive organ, and a similar examination can also be performed by performing a determination about a structure such as blood vessels in an inner portion via skin. In other words, as a specific target object to be detected, a lesion part in which a structure in a biological tissue can be observed from an outside of the biological tissue is raised as one candidate. The present invention is also capable of being practically applied to a case where a state of pigmentation of a mole, a melasma, or the like is diagnosed and whether the mole, the melasma, or the like is malignant is diagnosed, for example.

Figure 1:
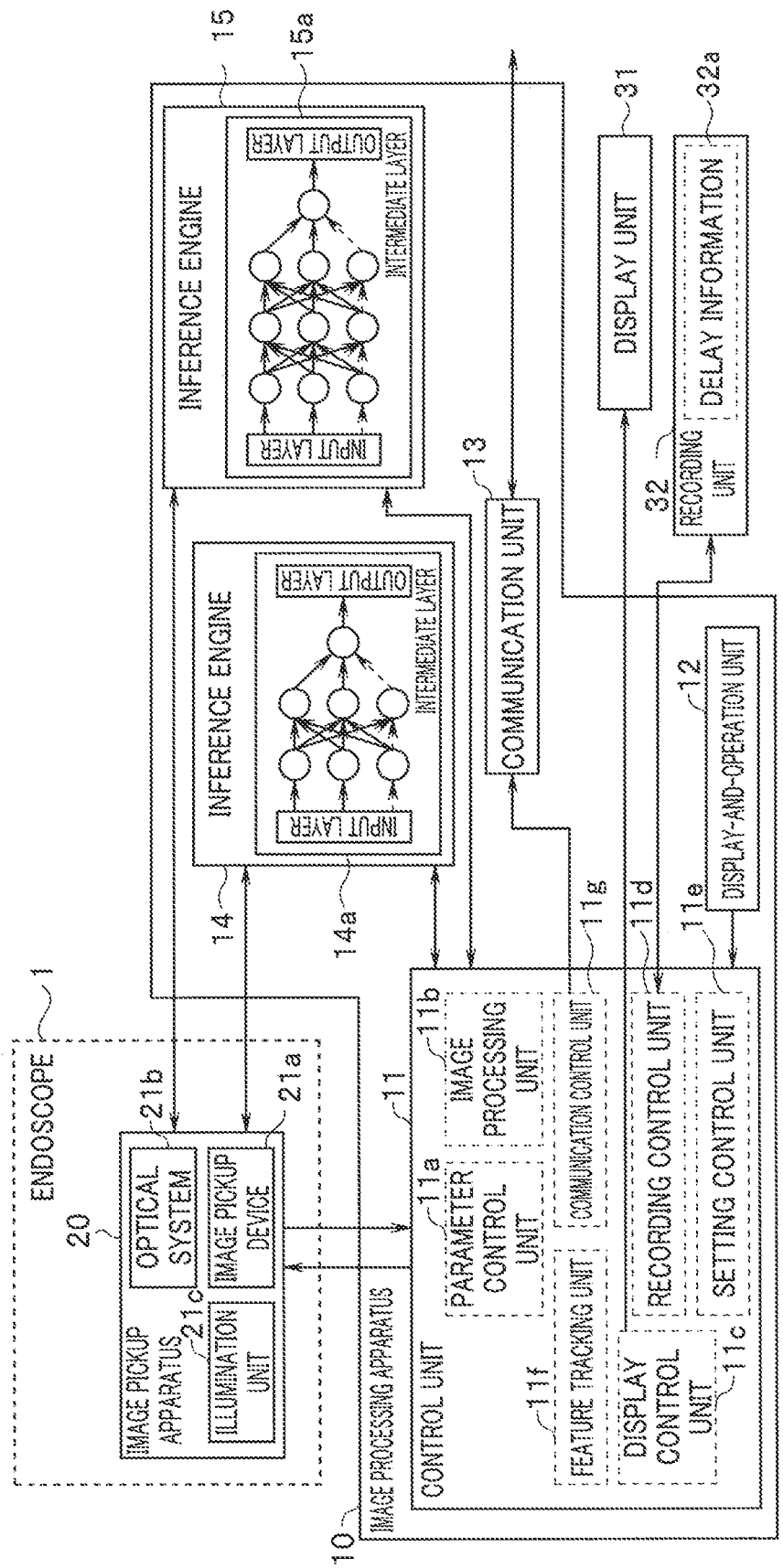
FIG. 1 is a block diagram illustrating an image processing apparatus according to a first embodiment of the present invention.

FIG. 1 is a block diagram illustrating an image processing apparatus according to a first embodiment (an endoscope is assumed to be used) of the present invention. In the present embodiment, plural inference models (two inference models in FIG. 1) are used while being switched in accordance with a predetermined condition, and a speed and precision of inference are thereby improved. As the predetermined condition for switching the inference models, for example, an image pickup condition in acquisition of an image as an inference target can be employed. In a case where various determinations by inference processing are performed for a picked-up image acquired in predetermined work, a certain determination may become possible by changing the image pickup conditions in accordance with work contents. In the present embodiment, inference models corresponding to work contents are prepared, the inference models are used while being switched in accordance with a change in the image pickup conditions, and optimal inference thereby becomes possible.

For example, in a case where the present embodiment is applied to a CAD which performs a diagnosis support using images photographed at a medical site, detection (finding) of a lesion part and discrimination about the lesion part are possible as use forms. As plural inference models, two inference models may be used, which are an inference model for detection (finding) of a lesion part and an inference model for discrimination for performing discrimination of a kind of a lesion part, between benign and malignant, and so forth about a detected lesion part.

When a lesion part in a lumen of a subject is detected, an endoscope inserted into the lumen is moved, and detection of a lesion part is performed by using images from an image pickup unit provided to the endoscope. In a case where discrimination is performed about the detected lesion part, a portion of the lesion part is observed by still images or the like, and an accurate diagnosis is thereby performed. Consequently, for example, an inference model suitable for high speed processing is prepared for finding, an inference model suitable for high precision processing is prepared for discrimination, the above inference models are used while being switched, and a high precision diagnosis thereby becomes possible. In the present embodiment, the switching is performed in accordance with the image pickup conditions.

In FIG. 1, an image from an image pickup apparatus 20 is given to an image processing apparatus 10. The image pickup apparatus 20 includes an image pickup device 21a and an optical system 21b. The optical system 21b may include lenses, an aperture, and so forth for zooming or focusing, which are not illustrated, and may include a zoom (magnification varying) mechanism and a focus-and-aperture mechanism which are configured to drive the lenses and are not illustrated. The optical system 21b guides a photographed object optical image to an image pickup surface of the image pickup device 21a. The image pickup device 21a is configured with a CCD, a CMOS sensor, or the like, performs photoelectric conversion of the photographed object optical image from the optical system 21b, and acquires a picked-up image (image-pickup signal) of a photographed object. Note that although FIG. 1 illustrates an example where the image pickup apparatus 20 is provided to an endoscope 1, the image pickup apparatus 20 may be configured in a shape or arrangement corresponding to the use form and is not limited to an image pickup apparatus provided to an endoscope.

In a case where the image pickup apparatus 20 illustrated in FIG. 1 is applied to an image pickup apparatus provided to the endoscope 1, the image pickup apparatus 20 may have an illumination unit 21c configured to illuminate an inner portion and so forth of a lumen. The illumination unit 21c produces illumination light, the subject is irradiated with the illumination light, and return light from the subject passes through the optical system 21b and is supplied to the image pickup device 21a. The illumination unit 21c has a predetermined light source such as an LED (light-emitting diode) which is not illustrated. For example, the illumination unit 21c may have plural light sources such as a light source configured to produce white light for a normal observation and a light source configured to produce narrow band light for a narrow band observation.

Note that although FIG. 1 illustrates the example where the illumination unit 21c is provided in the image pickup apparatus 20, a configuration may be made such that a light source apparatus not illustrated is provided on an outside of the image pickup apparatus 20, illumination light from the light source apparatus is guided to a vicinity of the photographed object by a light guide, and the photographed object is irradiated with the illumination light.

The image processing apparatus 10 includes a control unit 11 configured to control units of the image processing apparatus 10 and the image pickup apparatus 20. The control unit 11 as a second processor and units in the control units 11 may be configured with processors using a CPU (central processing unit), an FPGA (field programmable gate array), and so forth, and the control unit 11 may act following programs stored in a memory not illustrated and control the units and may realize a part or all of functions by an electronic circuit of hardware.

The control unit 11 includes a parameter control unit 11a configured to control the image pickup apparatus 20. The parameter control unit 11a controls the image pickup device 21a and thereby controls a frame rate, a gain, and so forth of a picked-up image. In a case where the optical system 21b has a zoom mechanism or the like, the parameter control unit 11a controls a mechanism of the optical system 21b. The parameter control unit 11a controls light emission of the light sources of the illumination unit 21c, adjusts respective light emission amounts of the light sources, produces white light in the normal observation, and produces narrow band light in a special observation using the narrow band light.

The control unit 11 takes in picked-up images (movies and still images) from the image pickup apparatus 20. An image processing unit 11b of the control unit 11 performs predetermined signal processing for the picked-up images which are taken in, for example, color adjustment processing, matrix conversion processing, noise removal processing, and various other signal processing.

A display-and-operation unit 12 is provided to the image processing apparatus 10, and a display control unit 11c is provided to the control unit 11. The display-and-operation unit 12 is a display device having a display screen such as an LCD (liquid crystal display apparatus), and the display screen is provided to a housing surface, for example, of the image processing apparatus 10. The display control unit 11c can cause a menu display or the like to be displayed on the display screen of the display-and-operation unit 12.

A touch panel not illustrated may be provided on the display screen of the display-and-operation unit 12. The touch panel as one example of an operation device can produce an operation signal corresponding to a position when a user indicates the position on the display screen by a finger. The operation signal is supplied to the control unit 11. Accordingly, the control unit 11 can detect the position, on the display screen, which is touched by the user and a sliding operation in which the user slides a finger on the display screen and can thereby execute processing corresponding to a user operation.

A picked-up image for which signal processing is performed by the image processing unit 11b is also given to the display control unit 11c. The display control unit 11c gives a picked-up image to the display unit 31 and causes the display unit 31 to display the picked-up image. The display unit 31 is a display device having a display screen such as an LCD. In the present embodiment, an inference result described later is given to the display control unit 11c, and the display control unit 11c can cause the display unit 31 to display the inference result. For example, the display control unit 11c can cause the display unit 31 to display an inference result which indicates a position of a lesion part on an image (observation image) from the image pickup apparatus 20 and a display of a discrimination result of a lesion part.

The control unit 11 is provided with a recording control unit 11d. The recording control unit 11d can perform compression processing for the picked-up image resulting from the signal processing, give the image resulting from compression to a recording unit 32, and cause the recording unit 32 to record the image. The recording unit 32 is configured with a predetermined recording medium and can record information given from the control unit 11 and output recorded information to the control unit 11. As the recording unit 32, a card interface may be employed, for example, and in such a case, the recording unit 32 is capable of recording image data in a recording medium such as a memory card.

The recording unit 32 has a region 32a configured to store information of a requirement specification which includes information of a detection time period required for inference processing, for example, and will be described later. As described later, the display control unit 11c can control an image display during inference by using the information of the detection time period.

The control unit 11 is provided with a setting control unit 11e. When information designating an observation mode or a support mode is given from the display-and-operation unit 12, the setting control unit 11e controls respective settings of the units of the control unit 11 in accordance with the information. For example, the setting control unit 11e may control the units such as the parameter control unit 11a such that the image pickup apparatus 20 performs a normal light observation in a finding mode and may control the units such as the parameter control unit 11a such that the image pickup apparatus 20 performs only a special light observation or both of the normal light observation and the special light observation in a discrimination mode.

The control unit 11 is provided with a feature tracking unit 11f. The feature tracking unit 11f is configured to track a specific target object included in a picked-up image from the image pickup apparatus 20 and to obtain a tracking result. The tracking result from the feature tracking unit 11f is given to the display control unit 11c. When an inference result is displayed, the display control unit 11c performs processing such as correcting a display position of the inference result based on the tracking result.

In the present embodiment, two inference engines 14 and 15 as first processors configured to perform inference are provided. The control unit 11 also gives picked-up images from the image pickup apparatus 20 to the inference engines 14 and 15. Images processed by the image processing unit 11b may be given to the inference engines 14 and 15. In inference in which priority is given to a high speed (in an input to the inference engine 14), an image may be input while processing is skipped as much as possible not via the image processing unit 11b, and in other cases, processed image data may be inputted to the inference engine 15 via the image processing unit 11b. Data from the image pickup device are inputted to the inference engine 15, information about processing is inputted from the control unit 11, and inference by multi-modal processing using image data and other data (such as supplemental data and correction data) may thereby be performed. The inference engines 14 and 15 perform inference by inference models corresponding to mutually different work contents (use forms). For example, in a case where the inference engines 14 and 15 are applied to the CAD, the inference engine 14 may be configured for finding of a lesion part, and the inference engine 15 may be configured for discrimination about a lesion part.

The inference engines 14 and 15 respectively have networks 14a and 15a. The networks 14a and 15a may be configured with hardware or may realize inference by software processing. A parameter for realizing predetermined inference processing is set for each of the networks 14a and 15a, and an inference model is constructed. A situation in which the inference models have different performance and specifications is illustrated while intermediate layers are changed as in FIGS. 1 and 2, but the numbers of layers do not necessarily have to be changed. However, the network 15a has restriction on data which can be dealt with, electric power, a time period used for processing, and so forth such that more specific inference can be performed than the network 14a and can perform more specific distinctions. A difference may be made by enabling the multi-modal processing to be performed by dealing with different information, separately from the above elements. A difference in specification may be such as a difference between an inference model configured to find a specific target object from all target objects and an inference model configured to obtain a result of further categorization of a specific target object. Note that in FIG. 1, network design such as the number of layers of the networks 14a and 15a is appropriately set. The inference models may be configured to be selectively actuated by the control unit 11, inputs may selectively be switched by a switch operation (not illustrated), and a configuration is possible in which the inference models are simultaneously actuated and obtain the same input and an output of the inference model with higher reliability can be selected.

A communication unit 13 is provided to the image processing apparatus 10, and a communication control unit 11g is provided to the control unit 11. The communication unit 13 is controlled by the communication control unit 11g and can transmit and receive information between a learning apparatus 40 and a learning request apparatus 50, which will be described later. The communication unit 13 is capable of short-distance wireless communication such as Bluetooth (registered trademark) and is capable of communication by a wireless LAN such as Wi-Fi (registered trademark). Note that the communication unit 13 is not limited to Bluetooth or Wi-Fi but is capable of employing communication by various communication systems. The communication control unit 11g can receive information (AI information) of an inference model from the learning apparatus 40 via the communication unit 13. The inference model information is for constructing desired inference models by the networks 14a and 15a of the inference engines 14 and 15.

The information of the inference models which is received by the communication unit 13 is supplied from the control unit 11 to the inference engines 14 and 15, and inference models are constructed in the networks 14a and 15a based on the information. The networks 14a and 15a receive inputs of picked-up images from the image pickup apparatus 20 and output inference results. For example, the network 14a outputs an inference result about a position of a lesion part, and the network 15a outputs an inference result about discrimination about a lesion part.

Because when a lesion part is found, inference processing has to be performed for picked-up images which are acquired while the image pickup apparatus 20 provided to the endoscope 1 is moved by an operation by a doctor or the like, usually, the inference processing has to be performed at a high speed. On the other hand, when whether or not oncogenic transformation occurs to a lesion part is discriminated, inference processing for performing a high precision determination by using still images or the like has to be performed. Consequently, between the inference engine 14 for finding and the inference engine 15 for discrimination, characteristics of inputted images such as resolution of inputted images (picked-up images), a frame rate, a magnification ratio, and an observation mode and requirements such as a detection speed (a processing time period necessary for inference) and reliability are mutually different. Consequently, network design is mutually different between the network 14a and the network 15a.

For example, the inference engine 14 for finding has to be set to a comparatively high detection speed, is preferably applied to comparatively low resolution, a comparatively high frame rate, a comparatively low magnification ratio, and a white light observation, and is possibly configured with comparatively small numbers of nodes (the number of channels of the intermediate layer, a filter size in convolution processing, and a step size corresponding to an interval in performing convolution processing) and of layers. On the other hand, the inference engine 15 for discrimination has to perform an accurate determination, is preferably applied to comparatively high resolution, a comparatively low frame rate, a comparatively high magnification ratio, and not only the white light observation but also the special light observation, and is possibly configured with comparatively large numbers of nodes and of layers. The expression of "comparatively" may be an expression with respect to a specific absolute value or may be a relative expression for a comparison about differences between both of the inference engines. For example, as for the frame rate and the speed, it is demanded that one of the inference engines should have such a speed that a response delay does not occur in a situation in which observation targets are sequentially changed or an observation target sequentially changes. Although a speed of several ten milliseconds or less is demanded, the speed may be changed depending on a target object or an operation speed of an operating person. Here, although an introduction is made by drawings in which an output from the image pickup device is directly inputted to the inference model, the output for which image processing is performed may be inputted to the inference model in accordance with necessity. In such a case, the output may be inputted to the inference model via the image processing unit 11b. In order to satisfy the requirement of speed, the numbers of intermediate layers of one inference model is of an order of several layers, for example, and the numbers of intermediate layers of the other inference model is of an order exceeding ten layers, for example.

Note that as the networks 14a and 15a, various known networks may be employed. R-CNN (regions with CNN features) using a CNN (convolutional neural network), FCN (fully convolutional networks), and so forth may be used. The known networks accompany processing referred to as "convolution" for compressing feature values of an image, act with minimum processing, and are strong in pattern recognition. A "recursive neural network" (fully connected recurrent neural net) may be used in which more complicated information can be dealt with and information flows in both directions in accordance with an information analysis, meanings of which are changed depending on order or a sequence.

In order to realize the above techniques, general-purpose arithmetic processing circuits such as a CPU and an FPGA may be used, but because many kinds of processing of neural networks are multiplication of matrices, there are cases where a GPU and an arithmetic processing circuit referred to as a tensor processing unit (TPU) are used, which are specialized in matrix calculation. In recent years, there have been cases where such "neural network processing unit (NPU)" of artificial intelligence (AI) dedicated hardware is designed to be capable of being incorporated in and of being integrated with other circuits such as a CPU and becomes a part of a processing circuit.

Figure 2:
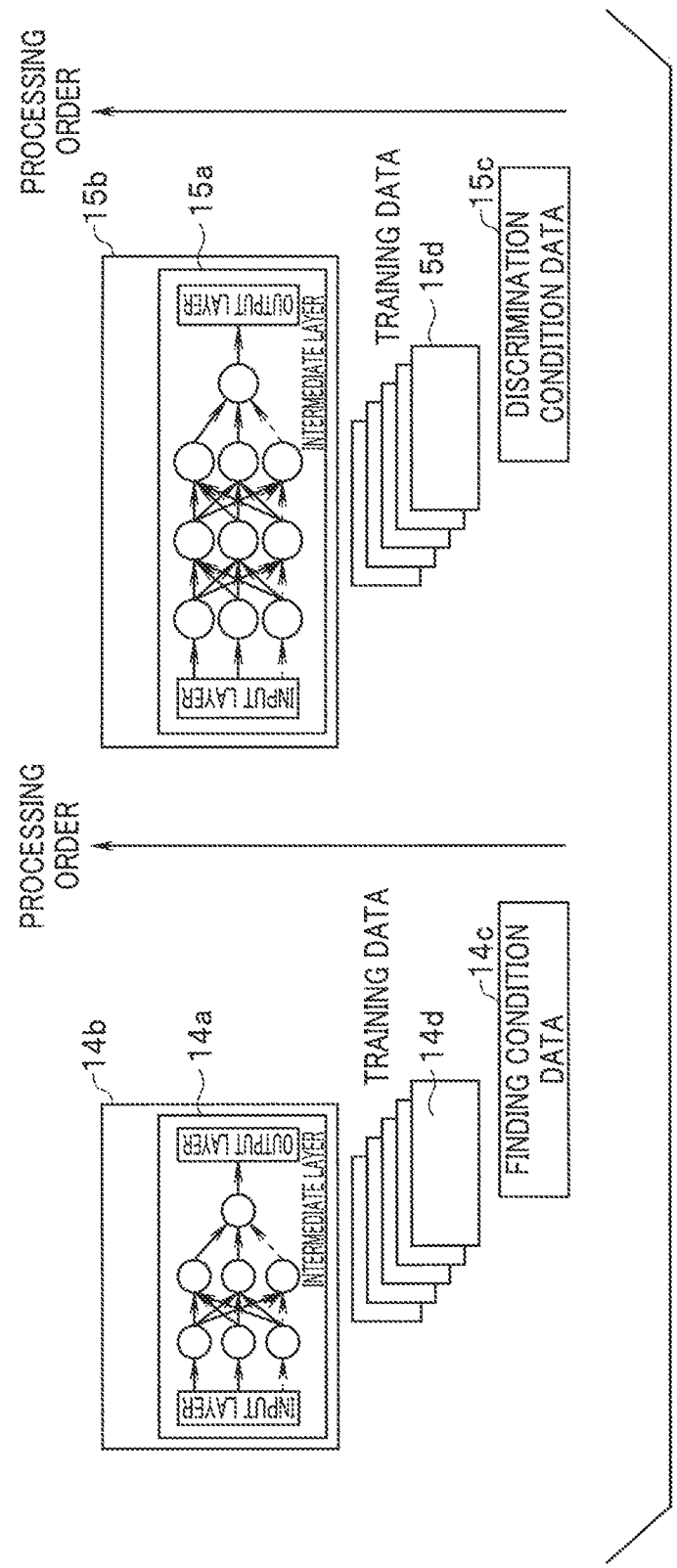
FIG. 2 is an explanatory diagram for explaining inference models used in inference engines 14 and 15.
Figure 3:
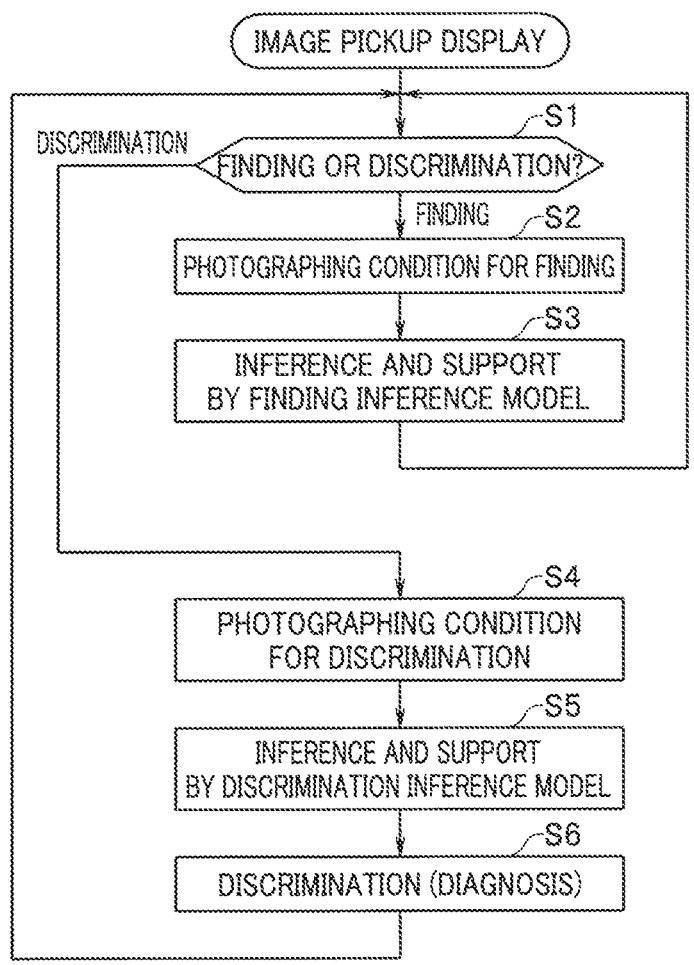
FIG. 3 is a flowchart for explaining an action in the first embodiment.

Next, an action in the embodiment configured in such a manner will be described with reference to FIG. 2. FIG. 2 is an explanatory diagram for explaining inference models used in the inference engines 14 and 15. FIG. 3 is a flowchart for explaining an action in the first embodiment. FIG. 3 illustrates display control for a diagnosis support in a case where the inference engine 14 is configured with the network 14a for finding of a lesion part and the inference engine 15 is configured with the network 15a for discrimination about a lesion part.

Here, in a case where detection (finding) and discrimination about a lesion part are considered to be use forms, the inference engine 14 is set for finding of a lesion part, and the inference engine 15 is set for discrimination about a lesion part. FIG. 2 illustrates learning phases of inference models 14b and 15b which construct the networks 14a and 15a of such inference engines 14 and 15. Arrows in FIG. 2 indicate order of processing, images are first selected from finding condition data 14c and discrimination condition data 15c, an expert such as a doctor adds annotations to respective images, and training data 14d and 15d are respectively created. Not only a method is possible in which a doctor creates training data, but also a method is possible in which a technician, a nurse, or AI creates candidates and a doctor checks the candidates. Then, learning is performed by using a known procedure by using the training data 14d and 15d. Note that the training data 14d and 15d may be used plural times in a process of learning. Data suitable for high speed processing are employed as the finding condition data 14c, and data suitable for high precision determination processing are employed as the discrimination condition data 15c.

What is important in FIG. 2 is the fact that respective specifications of the inference models 14b and 15b are different and requirement specifications of the inference models 14b and 15b are included, as information, in the condition data 14c and 15c. The inference model 14b for finding is suitable for high speed processing, for example, and employs the network 14a in which the number of nodes of an input layer, the number of layers, the number of pixels used for processing, and a data amount of intermediate layers are comparatively small, the training data 14d are given to the network 14a, and a parameter is thereby decided by learning. The inference model 15b for discrimination is suitable for high precision processing, for example, and employs the network 15a in which the number of nodes of an input layer and the number of layers are comparatively large, the training data 15d are given to the network 15a, and a parameter is thereby decided by learning.

For example, the inference model 14b for finding has to be set to a comparatively high detection speed, and images which are obtained at comparatively low resolution, a comparatively high frame rate (a processing time period is comparatively short, and for example, 1 frame of 30 fps can be handled depending on an image size), and a comparatively low magnification ratio, and obtained in the white light observation may be created as training data. On the other hand, the inference model 15b for discrimination has to perform accurate determinations, and images which are obtained at comparatively high resolution, a comparatively low frame rate (a processing time period is comparatively long, and for example, a time period corresponding to several frames of 30 fps is required depending on an image size), and a comparatively high magnification ratio, and obtained not only in the white light observation but also in the special light observation may be created as training data. Because accuracy is important in discrimination, when information on how assessment is performed is present, further assistance for the user becomes possible. When training data are created while being combined with such information, AI can be prevented from becoming a black box.

As described above, information of the decided inference models 14b and 15b is supplied to the inference engine 14 and the inference engine 15, and the networks 14a and 15a are constructed.

In step S1 in FIG. 3, the control unit 11 determines whether a current use form is finding of a lesion part or discrimination about a lesion part. For example, a practitioner is capable of designating whether a mode is a finding mode for finding a lesion part or a mode for performing discrimination by operating the display-and-operation unit 12. The control unit 11 is supplied with an operation signal based on an operation by the practitioner and determines whether the mode is the finding mode or a discrimination mode.

Here, it is assumed that the finding mode is designated. In such a case, the control unit 11 determines that the current use form is finding of a lesion part and sets the finding mode. For example, the parameter control unit 11a sets the image pickup condition of the image pickup apparatus 20 to an image pickup condition suitable for finding of a lesion part (step S2). For example, the parameter control unit 11a may perform settings for image pickup for the white light observation and at a high frame rate and a low image quality for the image pickup apparatus 20.

When such an image pickup condition is set, the control unit 11 employs the inference engine 14 as the inference engine used for inference. Picked-up images from the image pickup apparatus 20 are supplied to the inference engine 14, and the inference engine 14 performs inference processing by using the inference model for finding and gives an inference result to the control unit 11 (step S3). Inference by the inference engine 14 is suitable for high speed processing, and even in a case where the practitioner performs an observation of a subject while moving an endoscope insertion portion at a comparatively high speed, finding of a lesion part by the inference engine 14 is possible. The inference engine 14 sequentially outputs inference results to the control unit 11 (reliability data of the inference are also capable of being outputted). The control unit 11 decides display contents such that the display unit 31 displays the inference results and transmits a display control signal. For example, the display control unit 11c displays a display indicating information that a lesion part is present and a position of the lesion part on a picked-up image. When the display control unit 11c displays the inference result for finding by a conspicuous display such that the practitioner (operating person) easily finds the inference result, overlooking can be avoided. Trouble such as again performing an observation for finding a lesion part after starting a next operation can be omitted. Here, because quick transmission for helping switching of operation methods (such as stopping and returning) is important, the display may simply be visualization of a position, a range, and so forth and may simply be flashing of a display icon, color switching, and so forth. Because a position and a range are displayed, a superimposed display is performed. Because a notification of presence or absence may be performed for the practitioner (operating person), visual transmission can be replaced or supplemented by a sound, a vibration, or the like. Because when information such as reliability is outputted by characters, quick assessment is compromised for checking the characters, devising for simplifying information such as using different colors instead of characters is important.

When a lesion part is found, the practitioner designates the discrimination mode by the display-and-operation unit 12 for performing discrimination about the lesion part. The control unit 11 determines that the discrimination mode is designated by an operation signal from the display-and-operation unit 12. In such a case, the control unit 11 determines that the current use form is discrimination about a lesion part, transits from step S2 to step S4, and sets the discrimination mode. For example, the parameter control unit 11a sets the image pickup condition of the image pickup apparatus 20 to an image pickup condition suitable for discrimination about a lesion part (step S4). For example, the parameter control unit 11a may perform settings for image pickup for a narrow band light observation or combination use of the narrow band light observation and the white light observation, a low frame rate or a still image, a high image quality, and a comparatively high magnification ratio for the image pickup apparatus 20.

When such an image pickup condition is set, the control unit 11 employs the inference engine 15 as the inference engine used for inference. Picked-up images from the image pickup apparatus 20 are supplied to the inference engine 15, and the inference engine 15 performs inference processing by using the inference model for discrimination and gives an inference result to the control unit 11 (step S5). In such a case, reliability data of the inference is also capable of being outputted. Inference by the inference engine 15 is suitable for high precision processing, the practitioner stops movement of the endoscope insertion portion and performs an observation of a portion of the found lesion part, and discrimination about the lesion part by the inference engine 15 thereby becomes possible. The inference engine 15 sequentially outputs inference results to the control unit 11. The control unit 11 displays the inference results. For example, the display control unit 11c performs a display of a discrimination result on an image which is being picked up and includes the lesion part. Here, because the lesion part is accurately discriminated, a display visualizing not only simple position information but also a range or the like is preferable. Because a position and a range are displayed, a superimposed display is performed. In accordance with necessity, a specific reason for the discrimination may be displayed by characters. A portion which contributes to a decision of the discrimination may separately be displayed from a lesion range. Such devising makes possible a measure against "AI as a black box" which has been considered to be important in recent years. For example, a numerical value or the like of reliability may together be displayed. The practitioner refers to the display of the discrimination results obtained by inference and performs discrimination (diagnosis) about the images of the lesion part (step S6).

As described above, a display control apparatus can be provided which has inference units configured to perform inference from image pickup results by an image pickup unit by a first inference model for finding of a specific target object and by a second inference model for discrimination about the above specific target object, performs control such that the inference units are caused to execute inference by using the above first inference model and inference by the above second inference model, and includes a display control unit configured to display two inference results such that the above first inference and the above second inference are identifiable. The above display control unit makes an information amount of the display of the above first inference result different from an information amount of the display of the above second inference result in order to identifiably display a difference between the above first inference and the above second inference, thereby promotes immediate switching of operations by minimum necessary information for finding, specifically explains what the discrimination result is for discrimination, for example, and can secure urgency and certainty which are important on a spot.

Note that in the above description, a description is made about an example where the practitioner designates finding or discrimination of a lesion part, but the control unit 11 may use outputs of various sensors which include an image sensor and are not illustrated and may thereby determine whether the current use form is finding or discrimination of a lesion part. For example, in FIG. 3, a description is made about an example where the practitioner performs an operation for designating finding or discrimination and the control unit 11 thereby recognizes the current use form and changes image pickup conditions, but the control unit 11 may detect an operation for changing image pickup conditions by the practitioner and may thereby determines whether finding or discrimination is designated. For example, the practitioner performs an operation for changing image pickup conditions by operating the display-and-operation unit 12, and the control unit 11 may thereby recognize the use form. For example, control may be performed such that finding of a lesion is designated in a case where the practitioner selects the white light observation and discrimination about a lesion is designated in a case where the practitioner selects the narrow band light observation.

In a case where the control unit 11 detects movement of picked-up images from the image pickup apparatus 20 and a period in which a movement amount of images for a unit time period is smaller than a predetermined threshold value continues for a predetermined period or longer, for example, the control unit 11 may perform control such that a transition from finding to discrimination is performed.

Figure 4:
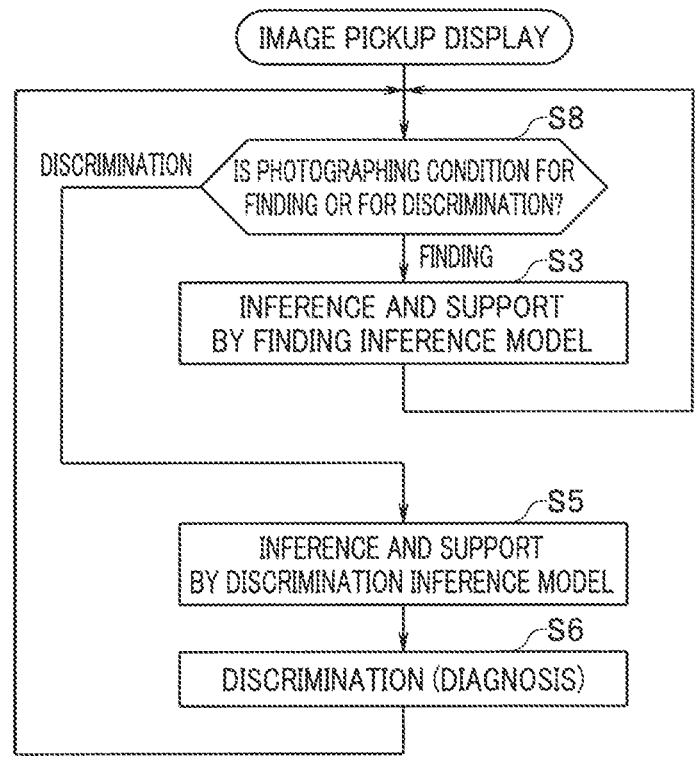
FIG. 4 is a flowchart illustrating that the inference models are changed when image pickup conditions are switched.

FIG. 4 is a flowchart illustrating that the inference models are changed when image pickup conditions are switched. In FIG. 4, the same reference characters are given to the same procedures as FIG. 3, and descriptions will not be made.

In a case where a diagnosis of a lesion part is performed, the finding mode is first conducted. The practitioner operates the display-and-operation unit 12 and sets an image pickup condition suitable for finding of a lesion part. The parameter control unit 11a sets the image pickup condition of the image pickup apparatus 20 to the image pickup condition suitable for finding of a lesion part. In step S8, the control unit 11 determines whether the image pickup condition is for finding or for discrimination. Accordingly, the control unit 11 causes processing to transit from step S8 to step S3 and employs the inference engine 14 as the inference engine used for inference.

When based on an operation for switching the image pickup condition to the image pickup condition for discrimination by the practitioner or on outputs from various sensors, the control unit 11 detects that the image pickup condition is changed to the image pickup condition for discrimination in step S8, the control unit 11 causes the processing to transit to step S5. Accordingly, the control unit 11 employs the inference engine 15 as the inference engine used for inference. Other workings are similar to FIG. 3. In such a case also, a display control apparatus can be provided which has inference units configured to perform inference from image pickup results by an image pickup unit by a first inference model for finding of a specific target object and by a second inference model for discrimination about the above specific target object, performs control such that the inference units are caused to execute inference by using the above first inference model and second inference model, and includes a display control unit configured to display two inference results such that the above first inference and the above second inference are identifiable. The above display control unit makes an information amount of the display of the above first inference result different from an information amount of the display of the above second inference result in order to identifiably display a difference between the above first inference and the above second inference, thereby promotes immediate switching of operations by minimum necessary information for finding, specifically explains what the discrimination result is for discrimination, for example, and can secure urgency and certainty which are important on a spot.

As described above, in either cases of FIG. 3 and FIG. 4, switching to the inference model for each use form is finally performed in accordance with a change of the image pickup condition, and inference is thereby performed.

Figure 5:
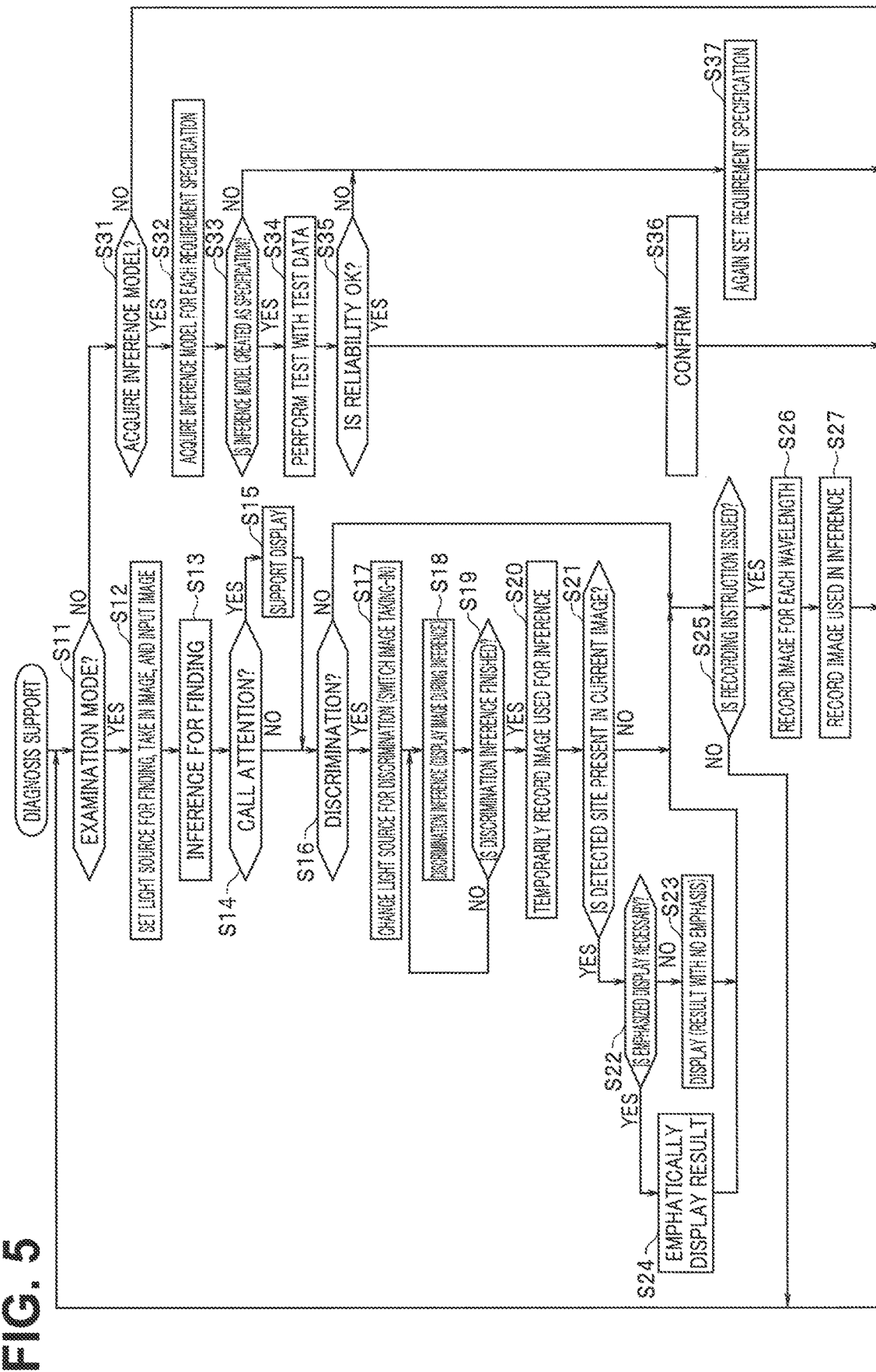
FIG. 5 is a flowchart illustrating a diagnosis support in the present embodiment.
Figure 6:
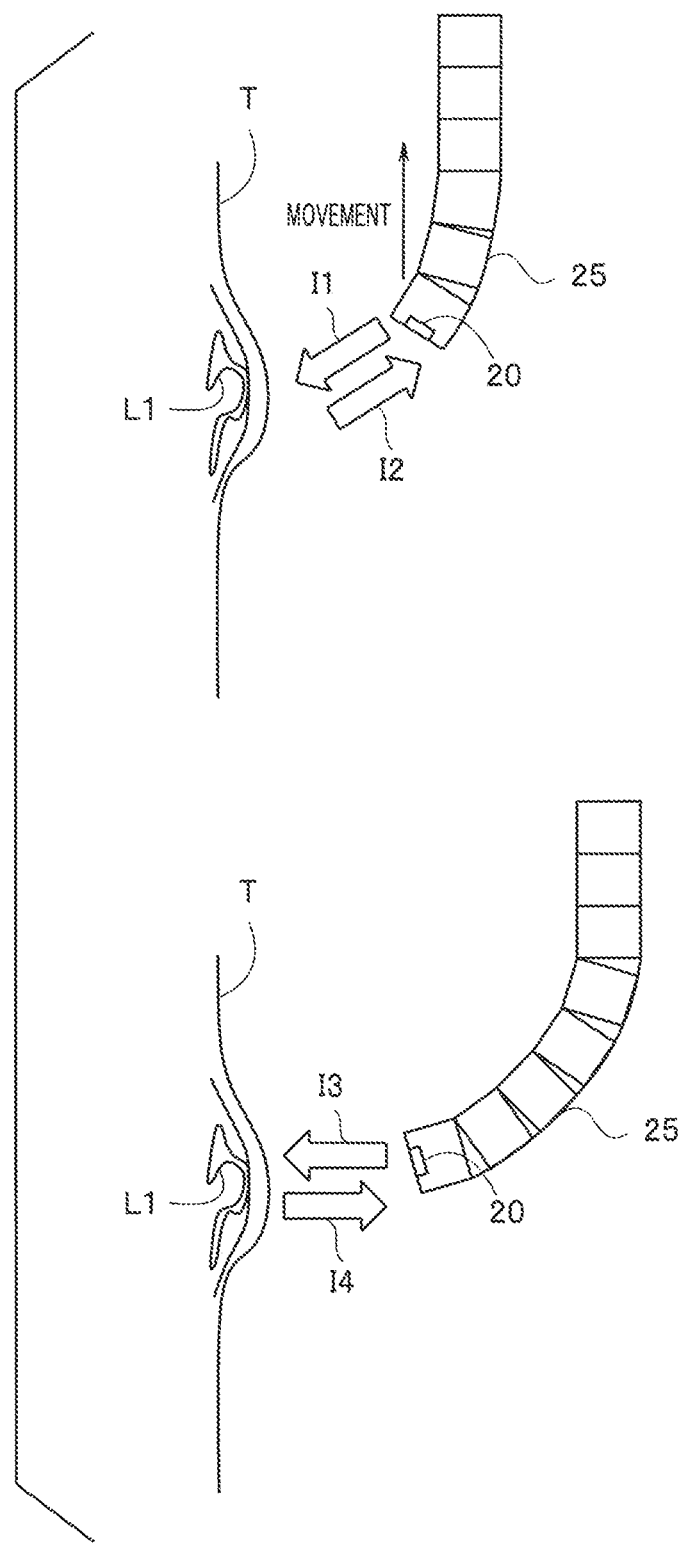
FIG. 6 is an explanatory diagram for explaining a situation of an examination.
Figure 7:
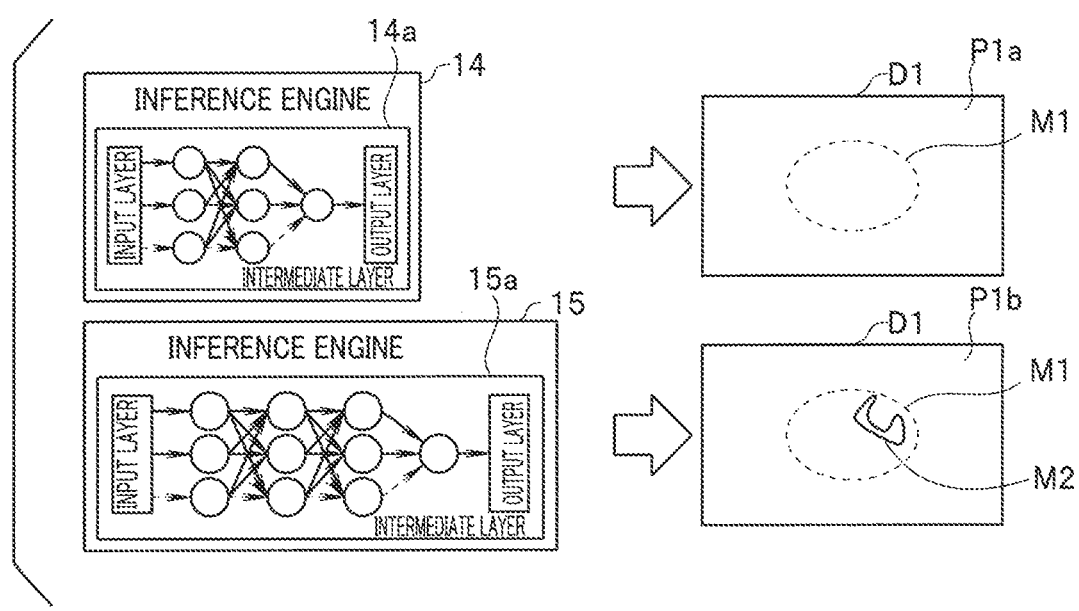
FIG. 7 is an explanatory diagram illustrating support displays obtained by inference processing.

Next, a specific example of a diagnosis support will be described with reference to FIG. 5 to FIG. 7. FIG. 5 is a flowchart illustrating the diagnosis support in the present embodiment. FIG. 6 is an explanatory diagram for explaining a situation of an examination. FIG. 7 is an explanatory diagram illustrating support displays obtained by inference processing.

In step S11 in FIG. 5, when an examination mode is designated, the control unit 11 first sets the finding mode. The parameter control unit 11 *a* sets the image pickup condition for finding for the image pickup apparatus 20 (step S12). For example, the parameter control unit 11*a* causes the illumination unit 21*c* to produce illumination light for finding and sets a comparatively high frame rate for the image pickup device 21*a*.

An upper stage of FIG. 6 illustrates a situation of image pickup in finding. In an example in FIG. 6, the image pickup apparatus 20 is mounted on a distal end of the endoscope insertion portion 25, and the image pickup apparatus 20 is capable of image pickup of an inner wall T surface of the subject. Note that a reference character L1 denotes a lesion part. The practitioner performs an observation of the inner wall T surface while moving the endoscope insertion portion 25 in arrow directions in FIG. 6, for example. The inner wall T surface is irradiated with illumination light I1 for finding from the image pickup apparatus 20, reflected light I2 from the inner wall T surface is guided to the image pickup surface of the image pickup device 21*a* by the optical system 21*b* of the image pickup apparatus 20. The image pickup apparatus 20 outputs picked-up images to the control unit 11 and the inference engine 14.

When processes to completion of finding and completion of finding and discrimination are described in relation to operations of an observation apparatus such as the endoscope, it can be understood that there is such a simple difference that movement of the observation apparatus for search is accompanied when finding is demanded but movement of the observation apparatus is not accompanied when discrimination is demanded. Presence or absence of movement can be determined based on changes in image pickup results. Using the changes, switching between the finding mode and the discrimination mode can be performed. Other than the above, a distinction between the finding mode and the discrimination mode is possible based on whether close approach is performed, whether an optical axis is generally orthogonally opposed to a target object surface, whether illuminations are switched, whether manual operations such as switching of focuses or focal distances and a magnification operation are performed, and so forth.

For example, as for a specific target object which moves, switching between the finding and discrimination modes is possible by a determination about movement of a target object (by comparing a speed, a form, an orientation, and so forth with a reference which is decided in advance). In other words, a practical application is performed such that watching is performed while the finding mode is started from an image in which movement is present so as not to disturb work during the work, in a case where a certain work mistake or a defect is noticed and work is stopped, the discrimination mode is started, and the nature of the problem is displayed.

As a case where the observation apparatus side moves similarly to the endoscope, practical application such as robot monitoring and monitoring by a wearable camera by a security officer are present. In such a case also, a camera side moves. There is of course a case where a camera side and a target object side also move. Determinations about whether an optical axis is generally orthogonally opposed to a target object surface, whether the observation apparatus approaches and stops, and so forth are determination methods which can be used in cases where the present invention is applied to other devices than an endoscope. An inference model for the mode switching may be prepared. To prepare such an inference model, a series of image group in which changes in scenes (a target object at certain time points) desired to be switched are photographed are learned as training data, and an inference model may thereby be created. Explaining a simple example, in photographing or the like of a bird, when an annotation for detection is added to a flying image and an annotation for discrimination is added to a stop image, various bird images with annotations are learned as training data, shapes of the bird in the bird images obtained by image pickup are used, an inference model for detection and tracking and an inference model for determining what the bird is can selectively be switched. In a case of following a bird, it is sufficient that the shape is known, but in a case where discrimination is performed about a kind of a bird, an image has to be an image in which information of a size of the bird, accurate distribution of colors of feathers, and so forth can be understood, and inference by an inference model different from an inference model in a case of tracking a bird is necessary. In inference using an inference model, image data obtained under a photographing condition in which features can be extracted are necessary, and appropriate image processing has to be applied to the images. In other words, an image processing apparatus is provided in which when it is assumed that a specific target object is an animal, images for a determination which are inputted to the above first inference model are images obtained under a photographing condition in which shapes of the above animal which is moving can be grasped, and images inputted to the above second inference model are images obtained under a photographing condition in which distribution of colors of the above animal can be grasped, and a camera can thereby be provided which is capable of tracking and identification. Such a concept is applicable not only to an animal but also a moving object, the above first and second inference models may be switched for a case where the control unit determines that a situation is a situation where a camera follows a moving object based on an output of a built-in acceleration sensor (or picked-up images) and for a case where the control unit determines that the camera does not follow the moving object but is in an aiming state based on the output of the built-in acceleration sensor (or picked-up images). Note that such switching is performed at a timing when a series of continuous images are taken in.

In the finding mode, inference by the inference engine 14 is performed (step S13). The inference model constructed in the inference engine 14 is capable of high speed processing and can correctly perform inference even when picked-up images are inputted at a comparatively high frame rate such as approximately 30 fps. Here, the inference engine 14 may perform inference at a frame rate different from a frame rate of the picked-up images but can preferably perform inference at the same frame rate (a shorter time period than a time period expressed by a reciprocal of the frame rate of the picked-up images). The inference engine 14 outputs inference results to the control unit 11.

In step S14, the control unit 11 determines whether or not attention of the practitioner has to be called due to finding of a lesion part. In a case where the inference result from the inference engine 14 indicates that a lesion part is found, the control unit 11 determines that attention of the practitioner has to be called, causes the processing to transit from step S14 to step S15, and causes the processing to transit to step S16 after the support display is performed. In such a case, unless information which has a small information amount but can instantaneously stop an operation is issued, the practitioner unconsciously changes places to be looked at and has difficulty in searching for a previous position. In a case where a lesion part is not found, in step S16, the control unit 11 determines whether or not a transition is performed to the discrimination mode.

An upper stage in FIG. 7 illustrates one example of inference by the inference engine 14 and an inference result. When a lesion part is found, the inference engine 14 outputs information of a position of the lesion part to the control unit 11. The display control unit 11c of the control unit 11 displays the inference result about the position of the lesion part while superimposing the inference result on the picked-up image. FIG. 7 illustrates that a picked-up image P1a from the image pickup apparatus 20 is displayed on a display screen D1 of the display unit 31 and a support display M1 indicating the position of the lesion part is displayed on the picked-up image P1a. Note that the support display M1 may be a rectangular shape other than an elliptical shape or may perform a flashing display of a marker or the like in a predetermined region (such as an upper right region) of the image.

In step S16, the control unit 11 determines whether or not the discrimination mode is designated. When the discrimination mode is designated, the control unit 11 sets the discrimination mode, and the parameter control unit 11a sets the image pickup condition for discrimination for the image pickup apparatus 20 (step S17). For example, the parameter control unit 11a causes the illumination unit 21c to produce illumination light for discrimination and sets a comparatively low frame rate for the image pickup device 21a or instructs the image pickup device 21a to photograph still images.

Note that the transition to the discrimination mode in step S16 may automatically be performed as described earlier. As for the determination about the transition to the discrimination mode and setting of the image pickup condition in steps S16 and S17, either one of pieces of processing may earlier be performed. For example, the practitioner changes the image pickup conditions, and the transition to the discrimination mode may thereby automatically be determined. For example, in a case where the practitioner recognizes that a lesion part is found by the support display in step S15, it is possible that the practitioner performs a release operation (still image acquisition operation) in order to perform discrimination about the lesion part. The control unit 11 may automatically transit to the discrimination mode by the release operation.

The control unit 11 may automatically transit to the discrimination mode by an operation (light source switching operation) for switching illumination light from the illumination unit 21c from illumination light for finding by white light to illumination light for discrimination by narrow band light, by an electronic zoom operation for magnifying a lesion part, by a focus switching operation, by an operation for bending the endoscope insertion portion 25 toward the lesion part L1, and so forth.

The control unit 11 may automatically transit to the discrimination mode in a case where the control unit 11 detects that movement of the acquired picked-up images is small or in a case where an inference result indicating that a lesion part is found by an inference result for finding is obtained.

A lower stage of FIG. 6 illustrates a situation of image pickup in discrimination. In discrimination, the practitioner moves the distal end portion of the endoscope insertion portion 25 to a vicinity of the position where the lesion part L1 is found, stops movement at the position (or while repeating movement and stops slowly and little by little, for example, or while moving the distal end portion at such a speed that a specific region is included in plural image frames sequentially obtained from the image pickup unit), and thereafter performs an observation of the inner wall T surface. In discrimination, the practitioner preferably causes the distal end portion of the endoscope insertion portion 25 to approach the lesion part L1 and thereby performs image pickup at a comparatively high magnification ratio. The inner wall T surface is irradiated with illumination light 13 for discrimination from the image pickup apparatus 20, reflected light 14 from the inner wall T surface is guided to the image pickup surface of the image pickup device 21a by the optical system 21b of the image pickup apparatus 20. The image pickup apparatus 20 outputs picked-up images to the control unit 11 and the inference engine 15.

In the discrimination mode, inference by the inference engine 15 is performed (step S18). The inference model constructed in the inference engine 15 is capable of high precision processing. Images inputted to the inference engine 15 are still images or images at a comparatively low frame rate such as several fps, and the inference engine 15 can perform certain inference by taking a comparatively long time period. Note that in a case where the images inputted to the inference engine 15 are made images at a higher speed than several fps, the inference engine 15 performs processing while thinning inputted frames. The inference engine 15 outputs inference results to the control unit 11. In step S19, the control unit 11 determines whether or not the inference for discrimination is finished and repeats inference in step S18 until the discrimination is finished.

When the inference is finished, in step S20, the control unit 11 temporarily records the images used for the inference. In next step S21, the control unit 11 determines whether or not an image portion of a detected site (lesion part L1) is present in a current screen. In a case where the detected site is not present in the screen in step S21 or in a case where the control unit 11 determines that the discrimination mode is not designated in step S16, the control unit 11 causes the processing to transit to next step S25 and determines whether or not a recording instruction is issued.

In a case where the lesion part L1 is positioned in the screen, the control unit 11 causes the processing to transit from step S21 to step S22 and determines whether or not an emphasized display is necessary. The emphasized display is performed in a case where malignancy of a lesion is high in the discrimination result, a case where the lesion is not at a center of the screen, and a case where the lesion is smaller than a predetermined area (size), for example. In a case where the emphasized display is not necessary, in step S23, the inference result is displayed (by the support display). Here, it is possible to display not only a position of a target object such as a lesion but also a range, and information of a reason for inference and reliability data may together be displayed. When the images can be recorded and maintained as still images, such information serves as evidences.

A lower stage in FIG. 7 illustrates one example of inference by the inference engine 15 and an inference result. When the discrimination about the found lesion part is finished, the inference engine 15 outputs discrimination results (inference results) to the control unit 11. The display control unit 11c of the control unit 11 displays the discrimination result (inference result) about the discriminated lesion part L1 while superimposing the discrimination result on the picked-up image. FIG. 7 illustrates that a picked-up image P1b from the image pickup apparatus 20 is displayed on the display screen D1 of the display unit 31 and the support display M1 indicating the position of the lesion part L1 and a support display M2 indicating that the lesion part found in the finding mode is a certain lesion as a result of the discrimination are displayed on the picked-up image P1b. Note that various inference results such as a disease name of the lesion part L1 and whether or not the lesion part L1 is subject to oncogenic transformation may be displayed by character strings or the like.

Note that the display control unit 11c displays the inference result about the lesion part L1 taking into consideration movement in the picked-up images. For example, in a case where an image used for discrimination is not a still image, the endoscope insertion portion 25 moves depending on an operation by the practitioner, and the position of the lesion part L1 on the image may be changed. Thus, the display control unit 11c decides display positions of the support displays M1 and M2 taking into consideration the movement of the picked-up images such that the display positions of the support displays M1 and M2 indicating the lesion part L1 come to correct positions on the displayed image.

In a case where the control unit 11 determines that an emphasis is necessary in step S22, the control unit 11 performs an emphasized display in step S24. For example, the display control unit 11c may color the lesion part L1 by a predetermined color, may put a predetermined pattern, or may display a character string or the like indicating the inference result in a conspicuous color or size. Note that in step S24 also, the control unit 11 displays the lesion part L1 in a correct position on the picked-up image taking into consideration the movement of the picked-up images.

Note that although a description is made on the assumption that the support displays indicating the inference results of discrimination are displayed on an image which is currently acquired, the support displays indicating the inference results of discrimination may be superimposed on an image which is temporarily recorded in step S20 and may thereby be displayed on the display screen D1 of the display unit 31. In such a case, even in a case where movement in the current picked-up image is comparatively large and the lesion part L1 is not present on the screen, a certain display becomes possible.

In a case where the recording control unit 11d of the control unit 11 determines that the recording instruction is present in step S25, in step S26, the recording control unit 11d categorizes the picked-up images acquired from the image pickup apparatus 20 in accordance with each wavelength of illumination light and records the categorized picked-up images in the recording unit 32. For example, the recording control unit 11d attaches information about wavelengths of illumination light to the picked-up images in the normal observation by white light and to the picked-up images in the special light observation by narrow band light and records the above picked-up images. In step S27, the recording control unit 11d also records the images used for the inference. The recorded images can be used for evidences, for example.

Incidentally, the control unit 11 can transmit information of specifications (hereinafter, referred to as requirement specification) about inference models to be constructed for the inference engines 14 and 15 to an external device not illustrated and can request creation of an inference model. In a case where the control unit 11 determines that the examination mode is not designated in step S11, the control unit 11 causes the processing to transit to step S31 and determines whether or not an inference model acquisition mode is designated. In a case where the inference model acquisition mode is not designated, the control unit 11 returns the processing to step S11.

In a case where the inference model acquisition mode is designated, in step S32, the control unit 11 acquires an inference model for each requirement specification. For example, in a case where the control unit 11 acquires an inference model set to the inference engine 14, the control unit 11 acquires information of an inference model corresponding to a requirement specification for finding, which is created by learning, from an external server not illustrated via the communication unit 13. For example, in a case where the control unit 11 acquires an inference model set to the inference engine 15, the control unit 11 acquires information of an inference model corresponding to a requirement specification for discrimination, which is created by learning, from an external server not illustrated via the communication unit 13.

In step S33, the control unit 11 determines whether or not the acquired inference model is created as the requirement specification. An inference model which satisfies the whole requirement specification cannot necessarily be obtained, and it is possible that performance such as a speed (detection speed) and precision is inadequate. There can be a case where performance is not suitable for a skill level of a practitioner (for example, an inference model with high sensitivity is often suitable for a beginner), a case where a combination of used devices does not ensure sufficient performance, a case where symptoms of a patient are known in advance but the inference model is not suitable for the symptoms, and so forth. In a case where the inference model is not creased as the requirement specification, the control unit 11 causes the processing to transit to step S37, again sets the requirement specification, thereafter transmits the specification to an external unit via the communication unit 13, requests learning of an inference model corresponding to the requirement specification, and thereafter returns the processing to step S11.

In a case where the control unit 11 determines that the inference model is created as the requirement specification, in step S34, the control unit 11 performs a test by using test data. Here, the test data may be recorded in advance in a test data recording unit not illustrated in the control unit 11 or may be acquired from an external unit (such as a storage or a private cloud in a medical facility) via the communication unit 13. The control unit 11 determines whether or not reliability of inference results obtained as a result of use of the test data is sufficiently high (step S35). In a case where the control unit 11 determines that the reliability is not sufficiently high, the processing is caused to transit to step S37, but in a case where the control unit 11 determines that the reliability is sufficiently high, the control unit 11 confirms that the inference model serves as the inference model for the inference engine 14 or 15 and returns the processing to step S11.

As described above, in the present embodiment, plural inference models corresponding to use forms are switched and used in accordance with the image pickup conditions, and inference results conforming to the use form can be obtained. For example, in a case where the inference models are applied to the diagnosis support for performing finding of and discrimination about a lesion part, the lesion part can be detected at a high speed, and it is possible to conduct highly precise discrimination about the lesion part.

Note that in the above description, a description is made about an example where the inference models for finding of and discrimination about a lesion part are prepared and the inference models are switched in response to switching between the image pickup condition for finding and the image pickup condition for discrimination, but it is clear that use forms are not limited to the above example.

Second Embodiment

Figure 8:
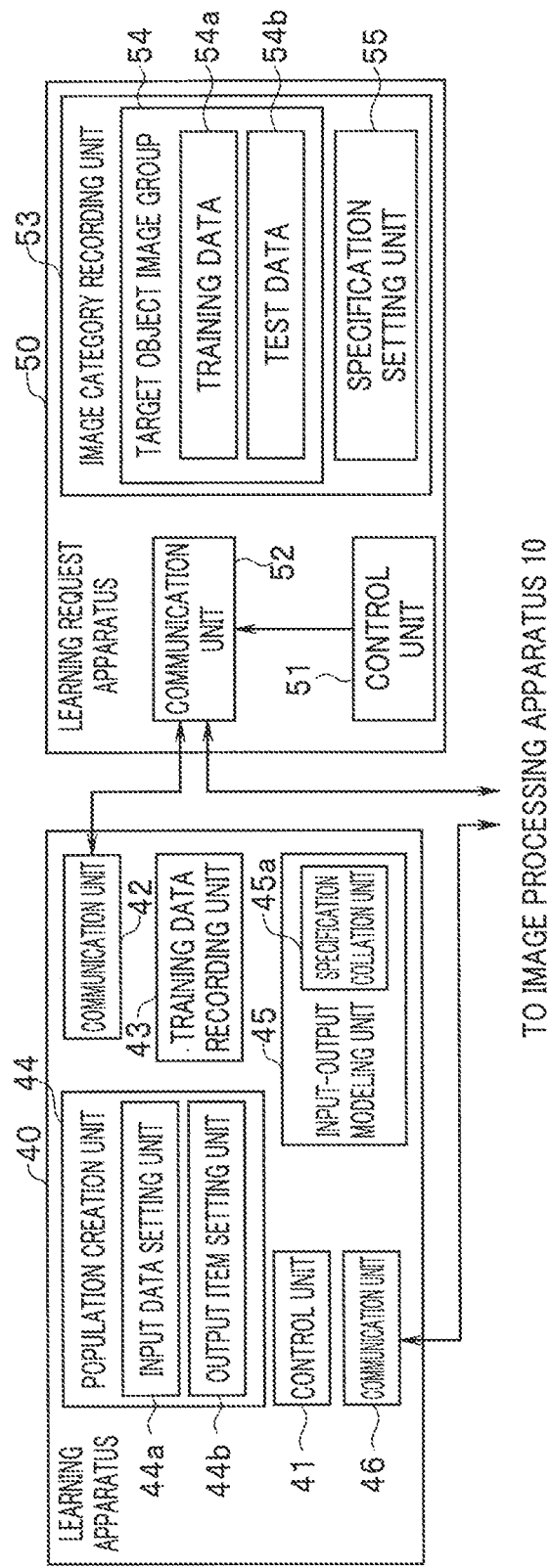
FIG. 8 is a block diagram illustrating a second embodiment of the present invention.

FIG. 8 is a block diagram illustrating a second embodiment of the present invention. In the present embodiment, a description will be made about a specific manner of creating the inference model which is employed in the first embodiment. In the present embodiment, the learning apparatus 40 creates the inference model, and the learning request apparatus 50 creates information necessary for learning in the learning apparatus 40 and supplies the information to the learning apparatus 40. Note that in the first embodiment, a description is made on the assumption that the control unit 11 in FIG. 1 outputs the information of the requirement specification of the inference model to an external device and requests creation of the inference model. In the present embodiment, the learning request apparatus 50 creates the requirement specification. The learning request apparatus 50 may be configured such that a specification setting unit 55 employs the requirement specification supplied from the control unit 11 in FIG. 1 without any change.

The learning request apparatus 50 has a communication unit 52, and the learning apparatus 40 has communication units 42 and 46. The communication units 42, 46, and 52 have a similar configuration to the communication unit 13 in the image processing apparatus 10 in FIG. 1, and mutual communication is possible between the communication units 13 and 46, between the communication units 13 and 52, and between the communication units 42 and 52. By the communication units 13, 42, 46, and 52, the information of the requirement specification from the image processing apparatus 10 in FIG. 1 can be supplied to the learning apparatus 40 and the learning request apparatus 50, and the image processing apparatus 10 can acquire the information of the inference model from the learning apparatus 40.

The learning request apparatus 50 has a control unit 51 configured to control units of the learning request apparatus 50, and the learning apparatus 40 has a control unit 41 configured to control units of the learning apparatus 40. The control units 41 and 51 may be configured with processors using a CPU, an FPGA, and so forth, may act following programs stored in a memory not illustrated and control the units, and may realize a part or all of functions by an electronic circuit of hardware.

Note that the whole learning apparatus 40 may be configured with a processor using a CPU, a GPU, an FPGA, or the like, may act following programs stored in a memory not illustrated and control learning, and may realize a part or all of functions by an electronic circuit of hardware.

The learning request apparatus 50 has an image category recording unit 53 configured to record a large amount of data for learning. The image category recording unit 53 is configured with a recording medium, not illustrated, such as a hard disk or a memory medium, categorizes plural images in accordance with each of kinds of target objects included in the images, and records the plural images. In an example in FIG. 8, the image category recording unit 53 stores a target object image group 54, and the target object image group 54 includes training data 54a and test data 54b for each of kinds of target objects. The control unit 51 follows a requirement from the learning apparatus 40, controls the communication unit 52, and transmits the training data 54a and the test data 54b to the learning apparatus 40. Note that the test data 54b are data resembling the training data 54a and are used for a test of an inference model obtained as a result of learning by the learning apparatus 40.

In the present embodiment, the learning request apparatus 50 is provided with the specification setting unit 55. The specification setting unit 55 decides the specification (requirement specification) of an inference model, and the image category recording unit 53 records training data and test data in accordance with the requirement specification defined by the specification setting unit 55. Note that the learning request apparatus 50 includes an input apparatus not illustrated and is thereby capable of an input of information about the requirement specification by a user operation. The learning request apparatus 50 may create requirement specification information based on information from the image processing apparatus 10 in FIG. 1.

The learning request apparatus 50 transmits learning request data including images of training data to the learning apparatus 40.

When the learning request data including images of training data are given from the learning request apparatus 50, the control unit 41 of the learning apparatus 40 records the training data in a training data recording unit 43. The training data recording unit 43 also records an inference model generated in the learning apparatus 40.

A population creation unit 44 of the learning apparatus 40 has an input data setting unit 44a and an output item setting unit 44b. The input data setting unit 44a sets input data (training data) used for learning, and the output item setting unit 44b sets an output to be obtained as a result of inference. Settings of the input data setting unit 44a and the output item setting unit 44b are performed based on the learning request data received from the learning request apparatus 50.

An input-output modeling unit 45 decides network design such that an expected output can be obtained from a large amount of training data and generates inference model information as setting information of the network design. Note that the network design is decided taking into consideration the requirement specification included in the learning request data from the learning request apparatus 50. The input-output modeling unit 45 is provided with a specification collation unit 45a. The specification collation unit 45a has a memory configured to store the learning request data and not illustrated and determines whether or not an inference model demanded by the input-output modeling unit 45 corresponds to the learning request data. The input-output modeling unit 45 performs construction of the network design (that is, selection or learning of plural networks which are set in advance) until the inference model becomes an inference model corresponding to the learning request data. Note that the network design decided in the input-output modeling unit 45 becomes network design to be employed for the inference engines 14 and 15 in FIG. 1.

The control unit 41 transmits information (AI information) of the inference model created in the input-output modeling unit 45 to the image processing apparatus 10 via the communication unit 13. The control unit 41 may give the generated inference model to the learning request apparatus 50 and cause the learning request apparatus 50 to record the inference model.

Figure 9:
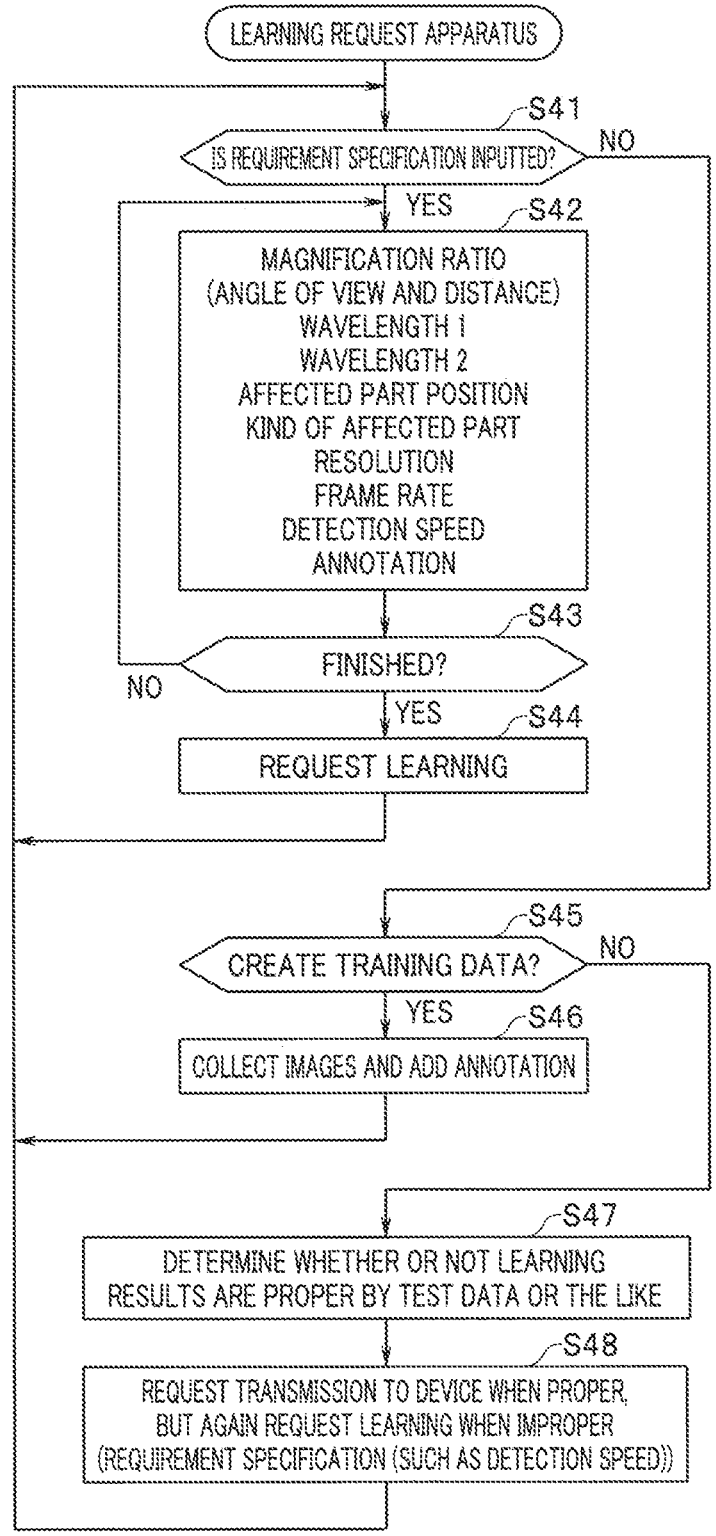
FIG. 9 is a flowchart illustrating an action of a learning request apparatus 50.
Figure 10:
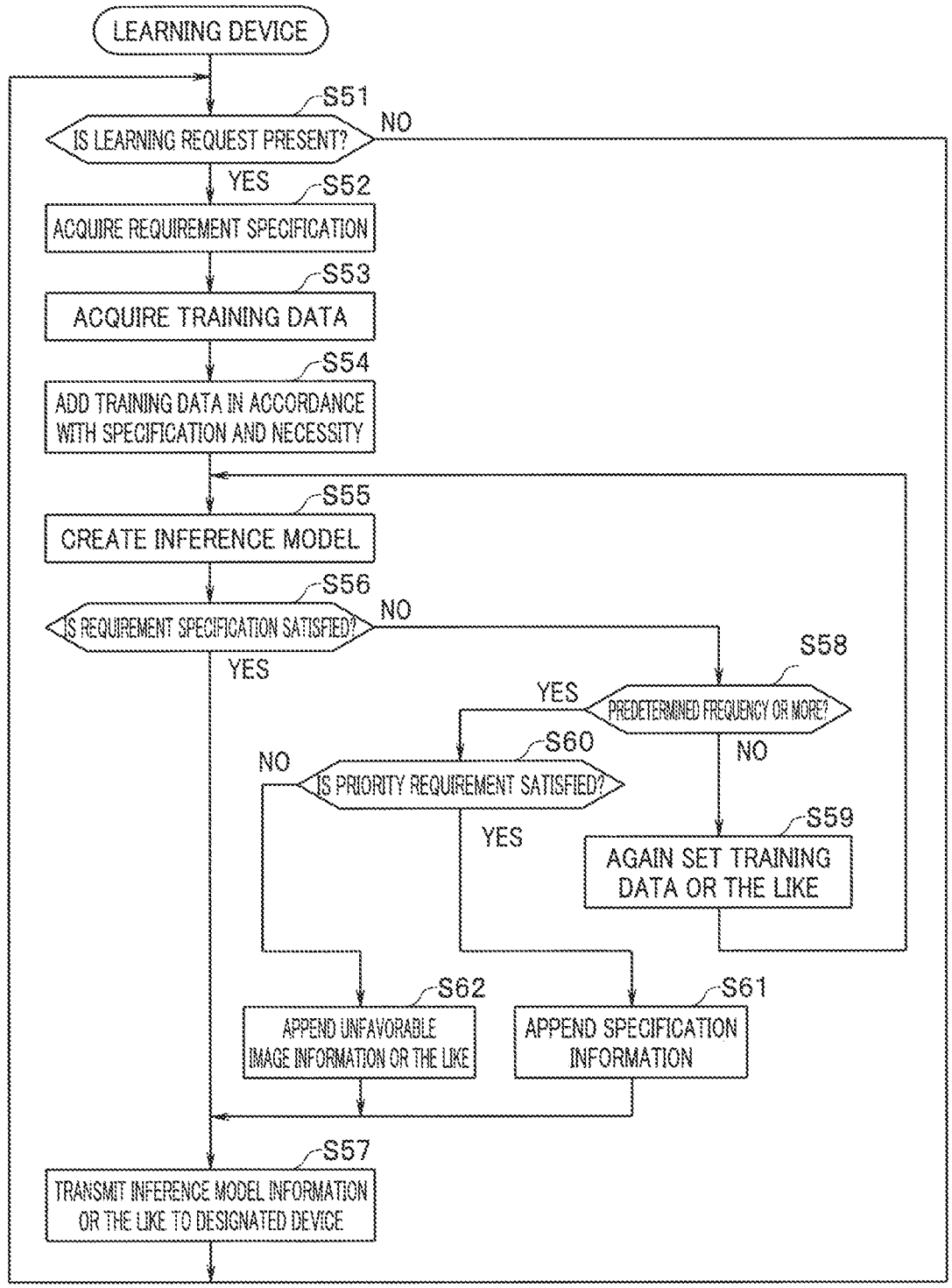
FIG. 10 is a flowchart illustrating an action of a learning apparatus 40.

Next, an action in the embodiment configured in such a manner will be described with reference to FIG. 9 and FIG. 10. FIG. 9 is a flowchart illustrating an action of the learning request apparatus 50, and FIG. 10 is a flowchart illustrating an action of the learning apparatus 40.

In step S41 in FIG. 9, the control unit 51 of the learning request apparatus 50 determines whether an input mode of the requirement specification is designated. In a case of the input mode of the requirement specification, in step S42, the specification setting unit 55 accepts an input of the requirement specification. In an example in FIG. 9, it is assumed that the use forms are finding of a lesion part and discrimination about a lesion part in the diagnosis support, and as the requirement specification, information is possible such as a magnification ratio, a wavelength, an affected part position, a kind of affected part, resolution, a frame rate, a detection speed, and an annotation.

For example, as the requirement specification necessary for construction of an inference model for finding of a lesion part, a comparatively low magnification ratio (a comparatively long distance from the image pickup device 21a to a photographed object and a comparatively narrow photographing range), a wavelength 1 of white light for the normal observation, comparatively low resolution, a comparatively high frame rate, and a comparatively high detection speed are set. The resolution corresponds to a data amount of an image dealt with, is thus directly connected with an image processing amount, and contributes to an increase in speed. Because the inference model is AI for preventing overlooking and natural images which matches a visual sense of the practitioner and are smooth are preferably obtained, requirements for performing learning in a specification in which a high frame rate, a high display speed, and so forth are important are set. Because such an operation that the practitioner is about to overlook a lesion part, returns, and again takes a look is performed, the inference model may be assisted by providing a recording function of features of detected parts. Accordingly, the inference model is provided with a tracking function for tracking a detected part such that it becomes possible to display an image in a direction in which a lesion part is overlooked. A "detection speed" is set as a specification which takes into consideration a time period to a display. Note that here, although a case is assumed where the endoscope detects features or the like of blood vessels under a mucosa, in a case where the present invention is practically applied, it is possible to provide similar overlooking prevention AI also for other target objects by preparing similar training data or requirement specification (a frame rate, a detection speed, and resolution) while detection objects to be dealt with are addressed.

As the requirement specification necessary for construction of an inference model for discrimination about a lesion part, a comparatively high magnification ratio (a comparatively short distance from the image pickup device 21a to a photographed object and a comparatively wide photographing range), wavelengths 1 and 2 of white light and narrow band light for not only the normal observation but also the narrow band observation, comparatively high resolution, a comparatively low frame rate, and a comparatively low detection speed are set. Note that affected part positions, kinds of affected parts, and so forth may be common to finding and discrimination.

Because resolution corresponds to a data amount of an image dealt with, although the resolution influences an image processing amount and a processing speed, in order to refer to fine features of an image here, the data amount, the resolution, and so forth are increased more than an inference model for detection. Further, for discrimination, such devising that a numerical value of reliability is displayed for making a careful check possible. It becomes possible for the practitioner to perform devising of image pickup increasing reliability while viewing the numerical value. Learning is performed which uses training data, in which the devising making such a display possible is performed and an annotation with position information that a certain image portion contributes to assessment is added, it is thereby possible to display a position of a site showing a reason in an image of a determination result, and it becomes possible to handle a demand for easiness of explanation about AI for a society.

Note that here, because a case is assumed where the endoscope detects features or the like of blood vessels under a mucosa, the first and second inference models are differentiated by wavelengths of the light sources, but in a case where the present invention is practically applied, differentiation of the inference models in accordance with the light sources are in general and often not necessary, and it is possible to provide similar overlooking prevention AI by preparing similar training data or requirement specification (a frame rate, a detection speed, and resolution) while detection objects to be dealt with are addressed. However, as for a monitoring camera or the like configured to perform a determination about a pattern of images of a dark target object by using infrared rays or the like, images photographed by infrared rays may be used as training data. In accordance with a speed, such devising becomes possible that images for which various image processing is performed are used as training data and detectability is improved by changing the image processing. Similarly, it is also possible to obtain an image for final discrimination by searching for a situation with high assessment reliability by changing exposures, focuses, and so forth. Learning may be performed by preparing training data corresponding to such a situation. In a case where such a scheme is selected, an inference model itself is divided into plural inference models, plural inference models are prepared which are caused to perform learning by preparing training data in which kinds of image processing or photographing conditions are changed for the same target object, images obtained by using the photographing conditions corresponding to the plural inference models and by conducting the corresponding kinds of image processing are inputted to each of the inference models, a comprehensive assessment is performed about the inference results, and information to be presented to the practitioner and an operator may thereby be decided.

Note that the specification setting unit 55 may set information of specifications of hardware of the inference engines 14 and 15 such as presence or absence of a GPU (graphic processing unit), presence or absence of an inference model dedicated circuit, the number of layers of a network, a clock frequency, and a memory capacity. The specification setting unit 55 may set kinds of the endoscope 1 (such as a thin endoscope or an endoscope having a high-pixel image pickup device), a specification of the image processing apparatus 10, characteristics of the light sources and the illumination unit 21, and so forth.

The control unit 51 determines whether or not setting of the requirement specification is finished in step S43, step S42 is continued until the setting is finished. When the setting is finished, in step S44, the control unit 51 creates the learning request data and requests the learning apparatus 40 to perform learning.

In a case where the control unit 51 determines that the input mode of the requirement specification is not designated in step S41, the control unit 51 causes the processing to transit to step S45 and determines whether or not a training data creation mode is designated. In a case where the training data creation mode is designated, in next step S46, the specification setting unit 55 creates a training data folder and a test data folder in the image category recording unit 53, collects images, and appends annotations. Although collection of images and appending of annotations are performed by an expert, an assistant may perform the collection and the appending before the expert makes decisions, and as assistance, AI may provide candidates and thereby make selection easy. In the phase of learning, an engineer creates inference models by sorting out training data, but an expert such as a doctor performs learning of the training data itself. In accordance with necessity, assistance by an inference model for annotations may be used. In other words, the specification setting unit 55 creates training data by adding annotations to a large amount of images including images which are obtained by image pickup under the image pickup conditions corresponding to the requirement specifications set in step S42 and causes the image category recording unit 53 to store the training data. Note that the specification setting unit 55 may create training data by using the requirement specification given from the image processing apparatus 10. The specification setting unit 55 creates the test data under a similar condition to the training data and causes the image category recording unit 53 to store the test data.

When processing in step S44 and S46 is finished, the control unit 51 performs the determinations in step S41 and S45, and in a case where the control unit 51 determines that neither of the requirement specification input mode nor the training data creation mode is designated, the control unit 51 causes the processing to transit to step S47 and performs a test for the inference model created by the learning apparatus 40. The control unit 51 determines whether learning results are proper or improper by using the test data stored in the image category recording unit 53. In a case where proper learning results are obtained in step S48, the control unit 51 request the learning apparatus 40 to transmit the created inference model to the image processing apparatus 10, but in a case where improper learning results are obtained, the control unit 51 again creates the learning request data based on the requirement specification such as the detection speed and requests the learning apparatus 40 to perform relearning.

Note that each piece of the processing by the learning request apparatus 50 can be similarly realized in the image processing apparatus 10.

In step S51 in FIG. 10, the control unit 41 of the learning apparatus 40 determines whether or not a learning request is present and becomes a stand-by state until the learning request is provided. When the learning request is produced, the control unit 41 acquires the requirement specification and the training data from the learning request apparatus 50 or the image processing apparatus 10 (step S52 and S53) and records the training data in the training data recording unit 43. In accordance with the requirement specification and necessity, the control unit 41 adds the training data by a known procedure such as data extension or by access to data accumulated in an external unit (step S54).

In step S55, the control unit 41 creates an inference model. In other words, the input-output modeling unit 45 reads out the training data from the training data recording unit 43, performs learning, and creates an inference model. Here, other than learning, plural pieces of network information are stored in advance in a storage region not illustrated, and a network may thereby be selected. In step S56, the specification collation unit 45a of the input-output modeling unit 45 determines whether or not the created inference model satisfies the requirement specification. For example, the specification collation unit 45a sets practice problems and performs verification of the created inference model (such as verification about whether predetermined precision is satisfied by conducting inference by using a part of learning data). In a case where the specification collation unit 45a determines that the reliability of inference is a predetermined value or more as a result of the verification using the practice problems, the control unit 41 determines that an inference model is correctly generated, transmits the inference model to the learning request apparatus 50 and the image processing apparatus 10 via the communication unit 46 (step S57), and returns the processing to step S51. Note that when the inference model is transmitted in step S57, the control unit 41 may transmit the inference model while appending specification information, particularly, specification information about a detection time period (detection speed).

In a case where the reliability is not the predetermined value or more, the input-output modeling unit 45 causes the processing to transit from step S56 to step S58 and again performs modeling by changing settings. The input-output modeling unit 45 determines whether or not a frequency of remodeling becomes a predetermined frequency or more (step S58), performs resetting of various parameters for training data or learning, reselection of network design, or the like in a case where the frequency is less than the predetermined frequency, thereafter returns the processing to step S55, and repeats creation of an inference model.

In a case where the resettings are performed at a predetermined frequency or more, the specification collation unit 45a of the input-output modeling unit 45 causes the processing to transit from step S58 to step S60 and determines whether or not the created inference model satisfies a specification to be given priority (priority requirement) in the requirement specification. In a case of satisfaction, in step S61, the input-output modeling unit 45 appends, to the inference model, information about an item which satisfies the requirement specification and an item which does not satisfy the requirement specification and thereafter transmits the inference model in step S57. In a case where the input-output modeling unit 45 determines that the priority requirement is not satisfied in step S60, the input-output modeling unit 45 appends information indicating that an inference model satisfying the requirement specification cannot be constructed, for example, information that images of the training data corresponding to the requirement specification are unfavorable images unsuitable for inference (unfavorable image information) (step S62), and thereafter transmits the information to the learning request apparatus 50 and the image processing apparatus 10 in step S57.

As described above, in the present embodiment, it is possible to construct an inference model which is suitable for each of finding of a lesion part and discrimination about a lesion part in the diagnosis support. Note that in the present embodiment, a description is made about an example where two inference models for finding of a lesion part and for discrimination about a lesion part are created, but it is clear that information of requirement specifications corresponding to use forms is generated, training data corresponding to the requirement specifications are created, and plural kinds of inference models corresponding to use forms can thereby be constructed.

Third Embodiment

FIG. 11 to FIG. 14 are explanatory diagrams for explaining a third embodiment. A hardware configuration in the present embodiment is similar to the first embodiment. Delays occur to displays of the diagnosis support for processing time periods (detection time periods) required for inference by the inference engines 14 and 15. In the present embodiment, even in a case where such delays occur, an effective diagnosis support is made possible.

Figure 11:
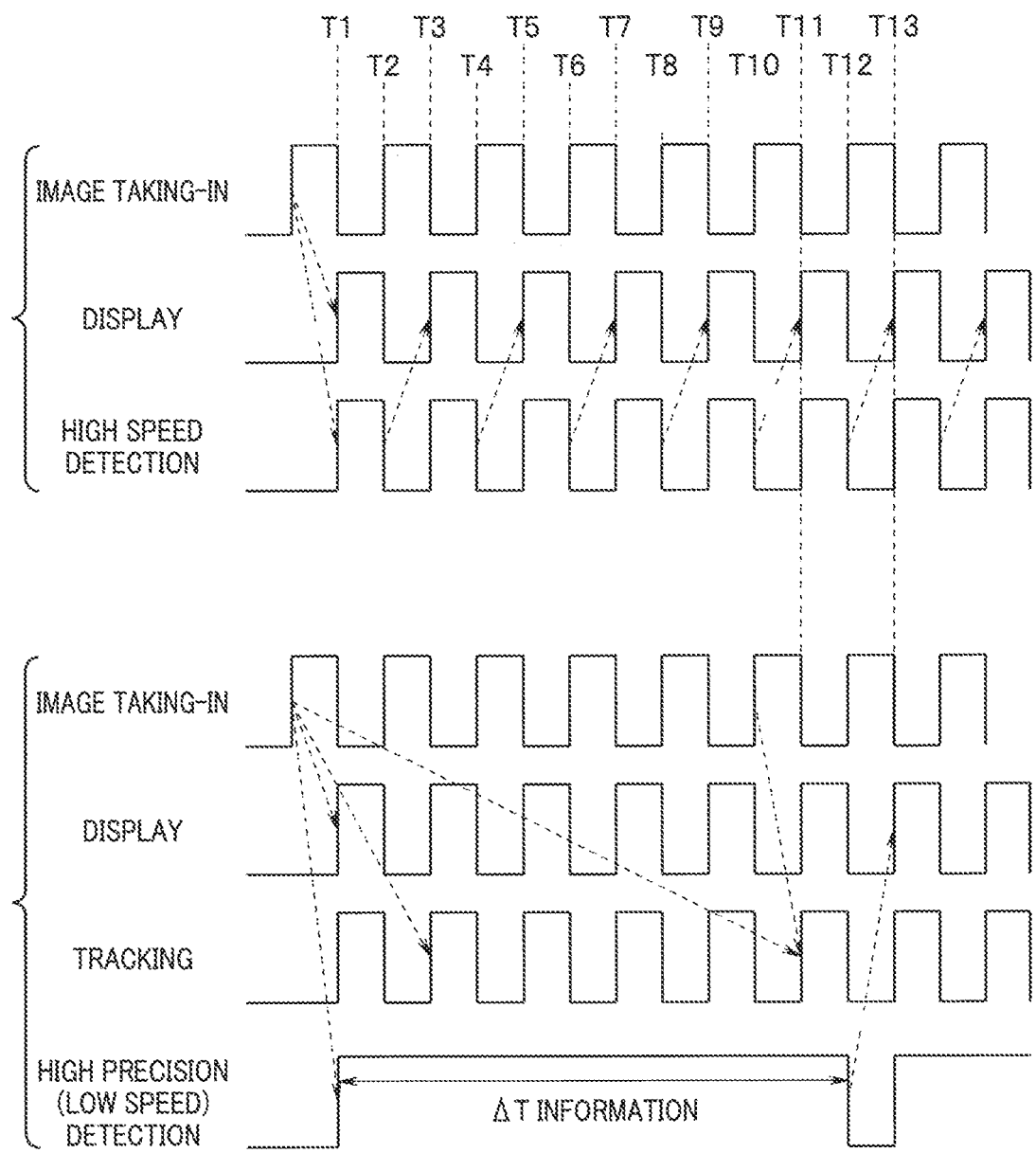
FIG. 11 is an explanatory diagram for explaining a third embodiment of the present invention.

An upper stage of FIG. 11 illustrates image taking-in timings, display timings, and inference detection timings in high speed detection in pulse shapes, and a lower stage of FIG. 11 illustrates image taking-in timings, display timings, tracking timings, and inference detection timings in high precision detection (low speed detection) in pulse shapes. Reference characters T1, T2, . . . in FIG. 11 indicate timings of 0.5-frame cycles of the picked-up images from the image pickup apparatus 20, and an example is illustrated where in either case of the high speed detection and the high precision detection, the frame rates of the picked-up images from the image pickup apparatus 20 are the same.

Respective images of frames are sequentially taken from the image pickup apparatus 20 into the image processing apparatus 10 and are supplied to the control unit 11 and the inference engine 14. In an example in FIG. 11, due to a delay time period of display control by the display control unit 11c, a display is started a 0.5-frame period after a start timing of image taking-in of each frame.

The upper stage in FIG. 11 illustrates an example where the inference engine 14 requires a one-frame period for inference processing, for example. In such a case, an inference result is displayed at a timing delayed by a one-frame period, for example, from the display of each frame image. In other words, the inference results corresponding to the frame images started being displayed at timings T1, T3, . . . are displayed while being superimposed on the picked-up images at timings T3, T5, . . . each of which is the timing later by one frame.

Also in the high precision detection illustrated in the lower stage in FIG. 11, the timings of displays are the same as the upper stage in FIG. 11. The lower stage in FIG. 11 illustrates an example where the inference engine 15 requires a five-frame period for inference processing, for example. Consequently, even in a shortest period, an inference result is displayed at a timing delayed by a five-frame period, for example, from the display of each frame image. Incidentally, in a case where the image pickup apparatus 20 moves with respect to a lesion part, the image position of the lesion part is changed around a five-frame period, and it is possible that the inference result cannot correctly be displayed. Consequently, in such a case, a more delay occurs for processing for detecting a movement amount of the picked-up images and for correcting the display position or the like of the inference result.

Accordingly, in the present embodiment, during inference processing by the inference engine 15, the movement amount of the picked-up images is already calculated. When a lesion part is found, the feature tracking unit 11f of the control unit 11 tracks the lesion part. A section of tracking in FIG. 11 indicates that the feature tracking unit 11f tracks a lesion part position in each frame. The control unit 11 uses tracking results to calculate a difference between a current image position of the lesion part and a position of the lesion part on the image as an inference target for each frame, for example. Note that the control unit 11 may predict the difference between the current image position of the lesion part and the position of the lesion part on the image as the inference target based on a time period ΔT required for the inference processing by the inference engine 15 and the tracking results.

The display control unit 11c display the inference result while superimposing the inference result on the image which is currently taken in and is displayed. Accordingly, a correct inference result is displayed at a timing delayed by a five-frame period, for example, with respect to the display of each frame image. In other words, the inference results corresponding to the frame images started being displayed at timings T1, T3, . . . are displayed while being superimposed in the correct positions on the picked-up images at timings T13, T15, . . . each of which is the timing later by five frames.

Figure 12A:
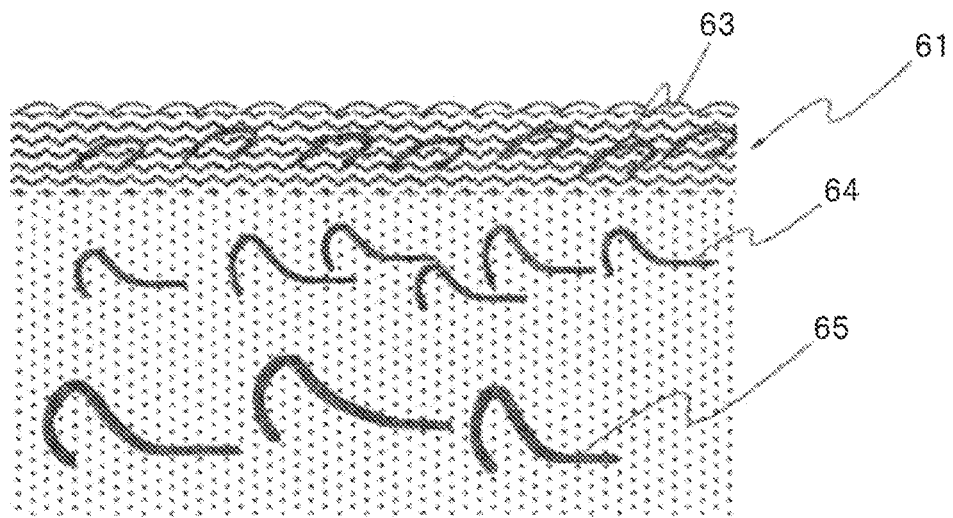
FIG. 12A is an explanatory diagram for explaining distribution of blood vessels in a body cavity inner tissue.
Figure 12B:
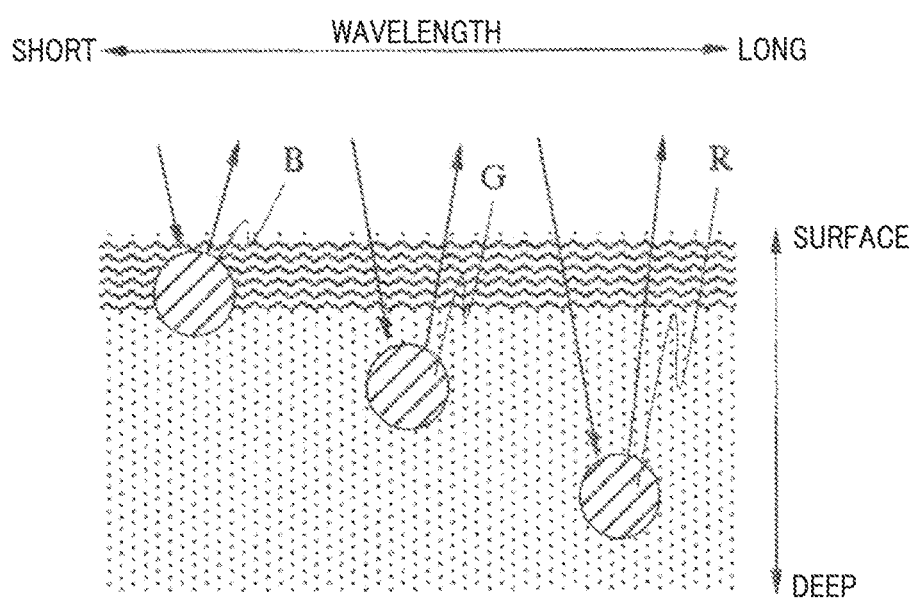
FIG. 12B is an explanatory diagram for explaining a reaching state of illumination light in a layer direction of biological tissues.
Figure 13:
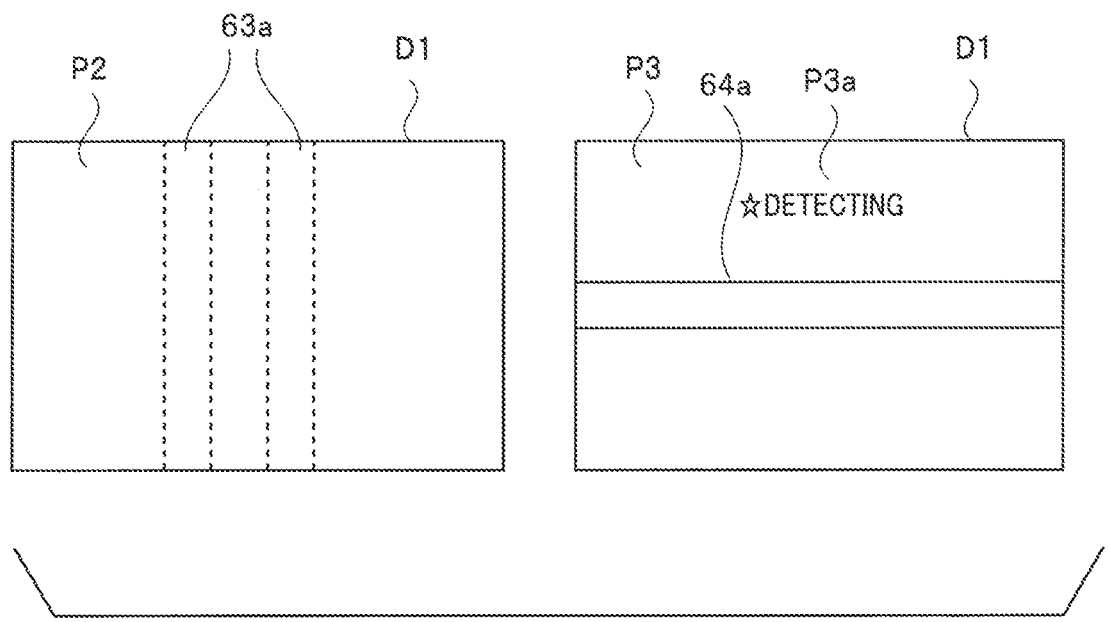
FIG. 13 is an explanatory diagram for explaining the third embodiment of the present invention.

FIG. 12A and FIG. 12B to FIG. 14 are for explaining displays in consideration of a delay due to inference and explain an example where the normal light observation is performed in finding of a lesion part in which high speed detection is performed and an observation by the narrow band light observation or by a combination of the narrow band light observation and the normal light observation is performed in discrimination about a lesion part in which high precision detection is performed. FIG. 12A is an explanatory diagram for explaining distribution of blood vessels in a body cavity inner tissue, and FIG. 12B is an explanatory diagram for explaining a reaching state of illumination light in a layer direction of biological tissues. FIG. 13 is an explanatory diagram illustrating picked-up images (observation images).

As illustrated in FIG. 12A, a body cavity inner tissue 61 often has an absorption-body distribution structures such as blood vessels different in a depth direction. Many capillary blood vessels 63 are mainly distributed around a mucosa surface layer, blood vessels 64 thicker than capillary blood vessels in addition to capillary blood vessels are distributed around a lower layer of a mucosa layer which is deeper than the above layer, and much thicker blood vessels 65 are distributed in a much deeper layer.

In a case where the body cavity inner tissue 61 is irradiated with illumination light and an observation is thereby performed, observation images change in accordance with penetration depths of light in a depth direction of the body cavity inner tissue 61. The penetration depths of light depend on wavelengths of light, and as illustrated in FIG. 12B, as for illumination light including a visible range, in a case of light at a short wavelength such as blue (B), the light penetrates only to a portion around a surface layer due to absorption characteristics and scattering characteristics in a biological tissue and is absorbed and scattered in a range at such a depth, and light emitted from a surface is observed. In a case of green (G) light at a longer wavelength than blue (B) light penetrates to a deeper place than the range to which the blue (B) light penetrates and is absorbed and scattered in the range, and light emitted from a surface is observed. As for red (R) light at a longer wavelength than the green (G) light, the light reaches a much deeper range.

For example, narrow band light at a wavelength of 415 nm (B light) and at a wavelength of 545 nm (G light) is likely to be absorbed by hemoglobin in blood vessels. Consequently, when an observation is performed by using narrow band light of B light and G light, a reflected light amount is lowered in portions of the capillary blood vessels 63 and the blood vessels 64 around a surface layer of a mucosa layer, the portions of the blood vessels 63 and 64 become dark portions on the picked-up images, and it becomes easy to distinct blood vessel shapes.

On the other hand, white light reaches the mucosa surface layer to blood vessels in a deeper layer and a mucosa in a much deeper layer and includes a wavelength band which is less absorbed by hemoglobin. Consequently, it is considered that with the picked-up images obtained by using white light, an observation of a surface of a body tissue is easy but blood vessel portions cannot clearly be observed. Consequently, in the normal light observation using white light, an observation of a surface of the body cavity inner tissue 61 is easy, and in the special light observation using the narrow band light, an observation of a surface layer of the body cavity inner tissue 61 to the blood vessels 63 and 64 or the like in comparatively shallow positions is easy.

A left side of FIG. 13 illustrates a display example in the white light observation, and a right side of FIG. 13 illustrates a display example in the narrow band light observation. In finding of a lesion part, the normal light observation is performed, and as indicated by broken lines in FIG. 13, a picked-up image P2 displayed on the display screen D1 of the display unit 31 includes images 63a which show the capillary blood vessels 63 in a not clear but blurry state. In discrimination about a lesion part, the narrow band light observation is performed, and a picked-up image P3 displayed on the display screen D1 includes an image 64a which shows the blood vessel 64 in a clear state. Because the inference processing in discrimination about a lesion part requires a comparatively long time period, the practitioner is possibly bewildered by viewing the picked-up image P3 in which a discrimination result does not appear for a certain time period.

Accordingly, in the present embodiment, the display control unit 11c displays a message display P3a of "detecting" in a lesion part discrimination. The practitioner can check that inference for discrimination about a lesion part is performed by the message display P3a.

FIG. 14 illustrates a display example where in discrimination about a lesion part, both of the normal light observation and the narrow band light observation are performed. An example of a case is illustrated where both of the blood vessels 63 and 64 can clearly be observed by using narrow band light such as B light and G light. A picked-up image P4 displayed on the display screen D1 illustrates a state where a lesion part indicated by a mark 65a is positioned at a general center of the screen. For example, in a case where a still image is used for inference, in a state where a lesion part found by inference of the inference engine 14 is positioned at a screen center, the picked-up image P4 as a still image can be acquired and used for discrimination inference. Consequently, in such a case, it is possible to perform a display of the mark 65a indicating a detected position of the lesion part and a display of a discrimination result not illustrated at the screen center of the display screen D1.

However, in a case where a movie is used for inference of discrimination about a lesion part, it is possible that a position of a lesion part on the display screen D1 is shifted from the center due to movement or the like of a hand of the practitioner. A picked-up image P5 in a lower left part in FIG. 14 illustrates a picked-up image in which such a position shift is present. Even in such a case, the tracking results of the feature tracking unit 11f are used, and the display control unit 11c can thereby certainly perform a display of a mark 65b indicating a detected position of a lesion part and a display of a discrimination result not illustrated.

A picked-up image P6 in a lower right part in FIG. 14 illustrates an example of a large position shift where movement of a picked-up image is comparatively large and an image portion of a lesion part deviates from a display region of the display screen D1. Note that broken lines 63b indicate a position of the capillary blood vessel 63, which is not displayed, on an outside of the screen. Even in such a case, the tracking results of the feature tracking unit 11f and detection results of movement of the picked-up images are used, and the display control unit 11c can thereby grasp that the detected position of the lesion part deviates from the display region of the display screen D1 and can perform a display of a mark 66 of "outside of screen" indicating that the lesion part deviates to the outside of the screen.

As described above, in the present embodiment, even in a case where a comparatively long time period is required for inference processing, it is possible to perform a display of an inference result which does not make the practitioner lost and which is easily understood by the practitioner, and an effect of making an effective diagnosis support possible is provided.

Note that the control units 11, 41, and 51, units of the learning apparatus 40, the specification setting unit 55, and so forth in the above embodiments may be configured with dedicated circuits or combinations of plural general-purpose circuits and may be configured, in accordance with necessity, by combining processors such as microprocessors and CPUs which perform actions following software programmed in advance and sequencers. Design is possible in which a part or all of control is undertaken by an external apparatus, and in such a case, a wired or wireless communication circuit is involved. An embodiment may be assumed in which feature processing or supplementary processing of the above embodiments are performed by an external device such as a server or a personal computer. In other words, a case where plural devices cooperate to establish features of the present invention is covered by the present application. For the communication in such a case, Bluetooth (registered trademark), Wi-Fi (registered trademark), telephone lines, and so forth are used. The communication in such a case may also be performed by a USB and so forth. Dedicated circuits, general-purpose circuits, and control units are integrated and may thereby be configured as an ASIC.

Among techniques explained herein, many pieces of control and functions mainly explained by the flowcharts can be set by programs, and the above-described control and functions can be realized by reading out and executing the programs by a computer. All or a part of the programs can be, as computer program products, recorded or stored in portable media such as non-volatile memories such as a flexible disk and a CD-ROM and storage media such as a hard disk and a volatile memory and can be distributed or provided by shipment of products or portable media or via communication lines. Users download the programs via communication networks and install the programs in computers or install in computers from recording media and can thereby easily realize the image processing apparatus of the present embodiments.

The present invention is not limited to the above embodiments without any change but may be embodied by modifying the configuration elements in phases of practice without departing from the scope of the gist of the present invention. Various embodiments may be formed by appropriately combining the plural configuration elements that are disclosed in the above embodiments. For example, several configuration elements among all of the configuration elements that are described in the above embodiments may be omitted. The configuration elements across the different embodiments may appropriately be combined. Herein, descriptions are made about examples of medical use, but as long as an inference model can be constructed for each use form in a series of pieces of work which includes different use forms, it goes without saying that the present invention is applicable to devices for consumer use, manufacturing use, and industrial use. For example, lesion finding AI can be considered to be AI configured to detect a certain abnormality, and lesion discrimination AI can be considered to be AI configured to minutely inspecting an abnormality. Such pieces of AI are AI capable of high speed processing and AI capable of high precision processing and can thus be used for first selection and second selection when cameras in steps make determinations about qualities of products flowing in a line in a factory or qualities of products during work. Alternatively, such pieces of AI can be applied to a system configured to switch monitoring AI which is used in movement while a wearable camera, a robot camera, or the like is used and monitoring AI which is used in a stop. Similarly, it is possible to practically apply such pieces of AI to an obstacle determination and so forth by a dashboard camera. For cameras for consumer use, use such as switching AI before and after a timing when a flying bird stops may be present. The present application is effective for a case where a wide range is sequentially magnified by a microscope.

What is claimed is:

1. An image processing apparatus comprising:
a memory device that stores an inference part; and
a control unit that performs a detection process based on the inference part, wherein:
the inference part is capable of inference by using a first inference model for finding of a specific target object and by using a second inference model for discrimination about the specific target object; and
the control unit is capable of receiving input of a first picked-up image obtained under a first image pickup condition and a second picked-up image obtained under a second image pickup condition different from the first image pickup condition and performing control such that in a case where the first picked-up image is inputted, the inference part is caused to execute inference by using the first inference model, and in a case where the second picked-up image is inputted,
the inference part is caused to execute inference by using the second inference model.

2. The image processing apparatus according to claim 1, wherein
the first inference model is designed such that a time period required for inference processing becomes shorter than the second inference model, and
the second inference model is designed such that precision of inference processing becomes higher than the first inference model.

3. The image processing apparatus according to claim 1, wherein
the second picked-up image is obtained by image pickup at a higher magnification ratio than the first picked-up image.

4. The image processing apparatus according to claim 1, wherein
the specific target object is a lesion part in which a structure in a biological tissue can be observed from an outside of the biological tissue, the first picked-up image is an image obtained by using white light as illumination light, and
the second picked-up image is an image obtained by using at least narrow band light as illumination light.

5. The image processing apparatus according to claim 1, wherein
the first inference model uses, as training data, images obtained by performing image pickup under the first image pickup condition, and
the second inference model uses, as training data, images obtained by performing image pickup under the second image pickup condition.

6. The image processing apparatus according to claim 1, wherein
the control unit performs display control for displaying the first picked-up image and the second picked-up image and display control for displaying a result of the inference by the inference part, and performs a display indicating that the inference by the second inference model is performed on the displayed second picked-up image in a period from a start of the inference by using the second inference model to a display of a result of the inference by the second inference model.

7. The image processing apparatus according to claim 1, wherein
the control unit detects movement of the second picked-up image and a position of the lesion part on the second picked-up image and
performs a position shift determination about a position of the lesion part at a time point when the inference part starts the inference by the second inference model and a position of the lesion part at a time point when the inference is finished.

8. The image processing apparatus according to claim 7, wherein
the control unit sets a display position of a result of the inference by the second inference model in accordance with a determination result of the position shift determination.

9. The image processing apparatus according to claim 1, wherein
the first inference model is designed to use, as training data, images obtained by performing image pickup by a first magnification ratio, illumination light of white light, and first resolution as the first image pickup condition, to perform inference of a position of a lesion part on the first picked-up image, and to obtain a result of the inference at a first detection speed, and
the second inference model is designed to use, as training data, images obtained by performing image pickup by a second magnification ratio higher than the first magnification ratio, illumination light of narrow band light, and second resolution greater than the first resolution as the second image pickup condition, to perform discrimination inference about a lesion part on the second picked-up image, and to obtain a result of the inference at a second detection speed which is a lower speed than the first detection speed.

10. An image processing apparatus comprising:
an inference part capable of inference by using a first inference model for tracking of a specific target object and by using a second inference model for identification of the specific target object; and
a control unit capable of receiving input of a first picked-up image obtained under a first image pickup condition and a second picked-up image obtained under a second image pickup condition different from the first image pickup condition and performing control such that in a case where the first picked-up image is inputted, the inference part is caused to execute inference by using the first inference model, and in case where the second picked-up image is inputted, the inference part is caused to execute inference by using the second inference model, wherein the specific target object is an animal, the first picked-up image is an image obtained under a photographing condition in which a shape of the animal in movement can be grasped, and the second picked-up image is an image obtained under a photographing condition in which distribution of colors of the animal can be grasped.

11. An endoscope apparatus comprising:

a control unit which acquires picked-up images obtained by an image pickup apparatus configured to perform image pickup by illuminating a target object and performs control such that the image pickup apparatus performs image pickup under a first image pickup condition and a second image pickup condition different from the first image pickup condition; and an inference part which performs inference by a first inference model for finding of the target object and by a second inference model for discrimination about the target object, wherein the control unit receives, from the image pickup apparatus, an input of a first picked-up image obtained by performing image pickup under a first illumination condition or the first image pickup condition and an input of a second picked-up image obtained by performing image pickup under a second illumination condition or the second image pickup condition and performs control such that in a case where the first picked-up image is inputted, the inference part is caused to execute the inference by using the first inference model, and in a case where the second picked-up image is inputted, the inference part is caused to execute the inference by using the second inference model.

12. An image processing method comprising:

receiving a first picked-up image obtained under a first image pickup condition or a second picked-up image obtained under a second image pickup condition different from the first image pickup condition; and performing control such that in a case where the first picked-up image is inputted, inference by using a first inference model for finding of a specific target object is caused to be executed, and in a case where a second picked-up image is inputted, inference by using a second inference model for discrimination about the specific target object is caused to be executed.

* * * * *